United States Patent [19]

Bradbury

[11] Patent Number: 5,373,015
[45] Date of Patent: Dec. 13, 1994

[54] FUSED PYRIDINE DERIVATIVES USEFUL AS ANGIOTENSIN II ANTAGONISTS

[75] Inventor: Robert H. Bradbury, Wilmslow, England

[73] Assignee: Imperial Chemical Industries PLC, London, England

[21] Appl. No.: 960,659

[22] Filed: Oct. 14, 1992

[30] Foreign Application Priority Data

Oct. 14, 1991 [GB] United Kingdom ............. 9121727.3

[51] Int. Cl.$^5$ ..................... A61K 31/44; C07D 471/04
[52] U.S. Cl. ..................................... 514/300; 546/122
[58] Field of Search ............... 546/113, 122, 123, 153, 546/156; 514/300, 312

[56] References Cited

U.S. PATENT DOCUMENTS

| | | | |
|---|---|---|---|
| 4,920,131 | 4/1990 | Huang et al. | 514/311 |
| 5,028,615 | 6/1991 | Huang et al. | 514/314 |
| 5,124,335 | 6/1992 | Patchett et al. | 514/300 |
| 5,126,344 | 6/1992 | Roberts et al. | 514/248 |
| 5,130,318 | 7/1992 | Roberts et al. | 514/299 |
| 5,246,944 | 9/1993 | Greenlee et al. | 514/312 |

FOREIGN PATENT DOCUMENTS

| | | |
|---|---|---|
| 0129408 | 12/1984 | European Pat. Off. |
| 0315399 | 5/1989 | European Pat. Off. |
| 0348155 | 12/1989 | European Pat. Off. |
| 0400974 | 12/1990 | European Pat. Off. |
| 0412848 | 2/1991 | European Pat. Off. |
| 0475206 | 3/1992 | European Pat. Off. |
| 0487745 | 6/1992 | European Pat. Off. |
| 0498721 | 8/1992 | European Pat. Off. |
| 0499415 | 8/1992 | European Pat. Off. |
| 0499416 | 8/1992 | European Pat. Off. |
| WO91/07404 | 5/1991 | WIPO. |
| WO91/11999 | 8/1991 | WIPO. |
| WO91/12001 | 8/1991 | WIPO. |

OTHER PUBLICATIONS

H. Gildemeister et al., "Neue 4-Chinolinol- und 5,6,7,8-Tetrahydro-4-chinoliol-abkommlinge mit biozider Wirkung", Liebigs Ann. Chem. 1982, 1656–1676.

P. Bellingham et al., "The Kinetics and Mechanism of Electrophilic Substitution of Heteoaromatic Compounds Part XV. Hydrogen Exchange of 3,5-Dimethylphenol and Heterocyclic Analogues", J. Chem. Soc. (B), 1968, pp. 866–873.

Ishibe et al., "Photoisomerization of 4-Pyridones to 2-Pyridones", Journal of the American Chemical Society, vol. 96, No. 4, Feb. 20, 1974, pp. 1152–1158.

Makabe et al., "A Convenient Synthesis of 1,4-Dihydro-4-Oxonicotinic Acid Derivatives", Heterocycles, vol. 13, 1979, pp. 239–246.

Hackler et al., "The Synthesis of 5-Amino-3-t-butylisothiazole and 3-Amino-5-butylisothiazole", J. Heterocyclic Chem. 26, 1575 (1989), pp. 1575–1578.

Veronese et al., "Tin (VI) Chloride-Promoted Reactions of β-Dicarbonyl Compounds with Nitriles. Synthesis of Aminopyridines and Aminoquinolenes". Tetrahedron Letters, vol. 31, No. 24, pp. 3485–3488, 1990.

Ziegler et al., "Synthesen Von Heterocyclen, 120, Mitt: 2,6-Dimethyl-4-pyridone dureh Reaktion von Enaminen Mit Diketen", Monatshefte fur Chemie 100, 132–135 (1969).

*Primary Examiner*—Marianne M. Cintins
*Assistant Examiner*—Phyllis G. Spivak
*Attorney, Agent, or Firm*—Cushman, Darby & Cushman

[57] ABSTRACT

The invention concerns pharmaceutically useful compounds of the formula I, in which Q, X, Z, $G^1$, $G^2$, $G^3$ and $G^4$ have the various meanings defined herein, and their non-toxic salts, and pharmaceutical compositions containing them. The novel compounds are of value in treating conditions such as hypertension and congestive heart failure.

9 Claims, No Drawings

FUSED PYRIDINE DERIVATIVES USEFUL AS ANGIOTENSIN II ANTAGONISTS

This invention concerns novel heterocyclic compounds and, more particularly, novel heterocyclic compounds which possess pharmacologically useful properties in antagonising at least in part one or more of the actions of the substances known as angiotensins, and in particular of that known as angiotensin II (hereinafter referred to as "AII"). The invention also concerns pharmaceutical compositions of the novel compounds for use in treating diseases or medical conditions such as hypertension, congestive heart failure and/or hyperaldosteronism in warm-blooded animals (including man), as well as in other diseases or medical conditions in which the renin-angiotensin-aldosterone system plays a significant causative role. The invention also includes processes for the manufacture of the novel compounds and their use in treating one of the afore-mentioned diseases or medical conditions and for the production of novel pharmaceuticals for use in such medical treatments.

The angiotensins are key mediators of the renin-angiotensin-aldosterone system, which is involved in the control of homeostasis and fluid/electrolyte balance in many warm-blooded animals, including man. The angiotensin known as AII is produced by the action of angiotensin converting enzyme (ACE) on angiotensin I, itself produced by the action of the enzyme renin on the blood plasma protein angiotensinogen. AII is a potent spasmogen especially in the vasculature and is known to increase vascular resistance and blood pressure. In addition, the angiotensins are known to stimulate the release of aldosterone and hence result in vascular congestion and hypertension via sodium and fluid retention mechanisms. Hitherto there have been a number of different approaches to pharmacological intervention in the renin-angiotensin-aldosterone system for therapeutic control of blood pressure and/or fluid/electrolyte balance, including, for example, inhibiting the actions of renin or ACE. However, there remains a continuing need for an alternative approach because of the side-effects and/or idiosyncratic reactions associated with any particular therapeutic approach.

We have now discovered that the compounds of the invention (set out below) surprisingly antagonise one or more of the actions of the substances known as angiotensins (and in particular of AII) and thus minimise the physiological effects associated with their presence in warm-blooded animals (including man) and this is the basis of the invention.

According to the invention there is provided a heterocyclic compound of the formula I (set out hereinafter, together with the other chemical formulae identified by Roman numerals) wherein Q is selected from a group of the partial structural formula IIa, IIb or IIc in which ring B of formula IIa completes a benzene or pyridine ring;

$R^1$ and $T^1$ are independently selected from (1–8C)alkyl, (3–8C)cycloalkyl, (3–8C)cycloalkyl-(1–4C)alkyl, phenyl, phenyl(1–4C)alkyl or substituted (1–4C)alkyl, the latter containing one or more fluoro substituents or bearing an (1–4C)alkoxy substituent;

$R^2$ and $T^2$ are independently selected from hydrogen, (1–8C)alkyl, (3–8C)cycloalkyl, (3–8C)cycloalkyl-(1–4C)alkyl, carboxy, (1–4C)alkoxycarbonyl, (3–6C)alkenyloxycarbonyl, cyano, nitro, phenyl or phenyl(1–4C)alkyl;

$R^3$ and $R^4$ are optional substituents on ring B independently selected from (1–4C)alkyl, (1–4C)alkoxy, halogeno, trifluoromethyl, cyano, nitro, fluoro(1–4C)alkoxy, hydroxy or hydroxy(1–4C)alkyl;

$T^3$ is selected from halogeno, (1–4C)alkoxy, amino, alkylamino and dialkylamino of up to 6 carbon atoms and any of the values defined for $T^1$;

$T^4$ is selected from hydrogen, (1–4C)alkyl, (1–4C)alkoxy, (1–4C)alkyl containing one or more fluoro substituents, carboxy, (1–4C)alkoxycarbonyl, (3–6C)alkenyloxycarbonyl, halogeno, cyano, nitro, carbamoyl, (1–4C)alkanoyl, N-alkylcarbamoyl and di-(N-alkyl)carbamoyl of up to 7 carbon atoms, amino, alkylamino and dialkylamino of up to 6 carbon atoms, and a group of the formula —$A^1.B^1$ wherein $A^1$ is (1–6C)alkylene, a carbonyl group or a direct bond and $B^1$ is (1) an unsubstituted phenyl or phenyl bearing one or two substituents independently selected from (1–4C)alkyl, (1–4C)alkoxy, halogeno, cyano, trifluoromethyl, nitro, hydroxy, carboxy, (1–4C)alkanoylamino, (1–4C)alkanoyl, fluoro(1–4C)alkoxy, hydroxy(1–4C)alkyl, (1–4C)alkoxy(1–4C)alkyl, carbamoyl, N-alkyl or di-(N-alkyl)carbamoyl of up to 7 carbon atoms, sulphamoyl, N-alkyl or di-(N-alkyl)sulphamoyl of up to 6 carbon atoms, (1–4C)alkoxycarbonyl, (1–4C)alkanesulphonamido, (1–4C)alkyl.$S(O)_n$— [in which n is zero, 1 or 2] and 1H-tetrazol-5-yl; or $B^1$ is (2) a 5 or 6-membered saturated or unsaturated heterocyclic ring optionally bearing a (1–4C)alkyl group and containing a single heteroatom selected from oxygen, sulphur and nitrogen or containing two heteroatoms one of which is nitrogen and the other is oxygen, sulphur or nitrogen;

or $T^3$ and $T^4$ together form an (3–6C)alkenylene group, an (3–6C)alkylene group or an (3–6C)alkylene group in which a methylene is replaced by carbonyl, provided that when $T^3$ and $T^4$ together form one of said latter three groups then $T^2$ is additionally selected from any of the previous values defined for $T^4$;

Y is oxygen or a group of the formula —NRb— wherein Rb is hydrogen, (1–4C)alkyl, (1–4C)alkanoyl or benzoyl;

linking group A of formula IIc is selected from —CH=CH—, —CH=CH—CO—, —CO—CH=CH—, —CO—CH$_2$—CH$_2$—, —CH$_2$—CH$_2$—CO, —CH$_2$—CO and —CO—CH$_2$—;

$E^1$ is hydrogen, (1–8C)alkyl or trifluoromethyl;

$E^2$ is hydrogen, (1–8C)alkyl, halogeno, (1–4C)alkoxy, trifluoromethyl, carboxy, (1–4C)alkoxycarbonyl, (3–6C)alkenyloxycarbonyl, cyano, nitro, (1–4C)alkanoyl, (1–4C)alkyl.$S(O)_m$— [in which m is zero, 1 or 2] or phenylsulphonyl;

$E^3$ is hydrogen, (1–8C)alkyl, (1–4C)alkoxy, halogeno or trifluoromethyl;

$E^4$ and $E^5$ are optional substituents on linking group A independently selected from (1–4C)alkyl, substituted (1–4C)alkyl containing one or more fluoro substituents, alkoxy, halogeno, cyano, nitro, carboxy, (1–4C)alkoxycarbonyl, (3–6C)alkenyloxycarbonyl, (1–4C)alkanoyl, carbamoyl, N-alkylcarbamoyl and di-(N-alkyl)carbamoyl of up to 7 carbon atoms, phenyl, pyridyl, phenylthio, phenylsulphinyl and phenylsulphonyl;

X is oxygen, sulphur or a group of the formula —NRc— wherein Rc is hydrogen or (1–4C)alkyl;

$G^1$, $G^2$, $G^3$ and $G^4$ are independently selected from hydrogen, (1–4C)alkyl, (1–4C)alkoxy and halogeno; Z is 1H-tetrazol-5-yl, carboxy or a group of the formula —CONHSO$_2$Ra wherein Ra is (1–4C)alkyl or phenyl; and wherein any of said phenyl moieties of $R^1$, $R^2$, $T^1$, $T^2$, $T^3$ or $E^2$ may be unsubstituted or bear one or two substituents independently selected from (1–4C)alkyl, (1–4C)alkoxy, halogeno, cyano and trifluoromethyl; or a non-toxic salt thereof.

It will appreciated that, in compounds of the formula I, the carbon atom to which Z is attached is asymmetric and hence, depending on the nature of the substituents present, compounds of the formula I will possess one or more chiral centres and will be isolated in one or more racemic or optically active forms. It is to be understood that this invention concerns any form of such a compound of formula I which possesses the afore-mentioned useful pharmacological properties, it being well known how to make optically active forms, for example by synthesis from suitable chiral intermediates, and how to determine their pharmacological properties, for example by use of the standard tests described hereinafter.

It is to be understood that generic terms such as "alkyl" include both straight and branched chain variants when the carbon numbers permit. However, when a particular radical such as "propyl" is given, it is specific to the straight chain variant, branched chain variants such as "isopropyl" being specifically named where intended. The same convention applies to other radicals.

A particular value for $R^1$, $R^2$, $T^1$ or $T^2$ where appropriate, include, by way of example, for alkyl: methyl, ethyl, propyl, butyl, isobutyl, sec-butyl, pentyl and hexyl;

for cycloalkyl: cyclopropyl, cyclopentyl and cyclohexyl;

for alkyl containing one or more fluoro substituents: fluoromethyl, trifluoromethyl, 2,2,2-trifluoroethyl and pentafluoroethyl;

for alkyl bearing an (1–4C)alkoxy substituent: 2-methoxyethyl and 2-ethoxyethyl;

for cycloalkyl-alkyl: cyclopropylmethyl, cyclopentylmethyl, cyclohexylmethyl and 2-cyclopentyl-ethyl;

for phenylalkyl: benzyl, 1-phenylethyl and 2-phenylethyl;

for alkoxycarbonyl: methoxycarbonyl, ethoxycarbonyl and propoxycarbonyl; and for alkenyloxycarbonyl: allyloxycarbonyl, 2-methyl-2-propenyloxycarbonyl and 3-methyl-3-butenyloxycarbonyl.

A particular value for $T^3$, $T^4$, or for $T^2$ when it is selected from a value for $T^4$, where appropriate, includes, by way of example, for alkyl: methyl, ethyl and propyl; for alkoxycarbonyl: methoxycarbonyl, ethoxycarbonyl and propoxycarbonyl; for alkenyloxycarbonyl: allyloxycarbonyl, 2-methyl-2-propenyloxycarbonyl and 3-methyl-3-butenyloxycarbonyl; for halogeno: fluoro, chloro, bromo and iodo; for alkoxy: methoxy, ethoxy and propoxy; for alkyl containing one or more fluoro substituents: fluoromethyl, trifluoromethyl, 2,2,2-trifluoroethyl and pentafluoroethyl; for alkanoyl: formyl, acetyl and butyryl; for N-alkylcarbamoyl: N-methyl and N-ethylcarbamoyl; for di(N-alkyl)carbamoyl: N,N-dimethylcarbamoyl and N,N-diethylcarbamoyl; for alkylamino: methylamino, ethylamino and butylamino; and for dialkylamino: dimethylamino, diethylamino and dipropylamino.

A particular value for $A^1$ when it is alkylene is, for example, methylene, ethylene or propylene.

Particular values for $R^3$, $R^4$ or an optional substituent on $B^1$ when it is phenyl bearing one or two substituents, where appropriate, include, by way of example, for alkyl: methyl and ethyl; for alkoxy: methoxy and ethoxy; for halogeno: chloro, bromo and iodo; for alkanoylamino: formamido, acetamido and propanamido; for alkanoyl: formyl, acetyl and butyryl; for fluoroalkoxy: trifluoromethoxy, 2-fluoroethoxy, 2,2,2-trifluoroethoxy and 3,3,3-trifluoropropoxy; for hydroxyalkyl: hydroxymethyl, 1-hydroxyethyl and 2-hydroxyethyl; for alkoxyalkyl: 2-methoxyethyl and 2-ethoxyethyl; for N-alkylcarbamoyl: N-methyl and N-ethylcarbamoyl; for di(N-alkyl)carbamoyl: N,N-dimethylcarbamoyl and N,N-diethylcarbamoyl; for N-alkylsulphamoyl: N-methyl and Nethylsulphamoyl; for di(N-alkylsulphamoyl: N,N-dimethylsulphamoyl and N,N-diethylsulphamoyl; for alkoxycarbonyl: methoxycarbonyl, ethoxycarbonyl and propoxycarbonyl; for alkanesulphonamido: methanesulphonamido and ethanesulphonamido; for alkylthio: methylthio and ethylthio; for alkylsulphinyl: methylsulphinyl and ethylsulphinyl; and for alkylsulphonyl: methylsulphonyl and ethylsulphonyl.

A particular value for $B^1$ when it is a 5 or 6-membered saturated or unsaturated heterocyclic ring containing a single hetero atom selected from oxygen, sulphur or nitrogen includes, for example, a thienyl, furyl, pyrrolyl, pyrrolidinyl, pyridyl and piperidyl ring.

A particular value for $B^1$ when it is a 5 or 6-membered saturated or unsaturated heterocyclic ring containing two heteroatoms one of which is nitrogen and the other is oxygen, sulphur or nitrogen includes, for example, an imidazolyl, imidazolidinyl, pyrazolyl, pyrazolinyl, thiazolyl, thiazolinyl, oxazolyl, oxazolidinyl, pyrimidinyl, pyrazinyl, pyridazinyl, piperazinyl, morpholinyl and thiomorpholinyl ring.

A particular value for an alkyl group which may be present on $B^1$ when it is a saturated or unsaturated heterocyclic ring is, for example, methyl or ethyl.

A particular value for $T^3$ and $T^4$ when together they form (3–6C)alkylene is, for example, trimethylene, tetramethylene or pentamethylene; when together they form (3–6C)alkenylene is, for example, 1-propenylene, 2-propenylene, 1-butenylene, 2-butenylene or 3-butenylene; and when together they form (3–6C)alkylene wherein one of the methylene groups is replaced by a carbonyl group is, for example, 1-oxopropylidene, 3-oxopropylidene, 1-oxobutylidene or 4-oxobutylidene.

A particular value for Rb when it is alkyl is, for example, methyl or ethyl; and when it is alkanoyl is, for example, formyl, acetyl or propanoyl.

A particular value for $E^1$, $E^2$ or $E^3$ when it is alkyl is, for example, methyl, ethyl, propyl, butyl, isobutyl, sec-butyl, pentyl or hexyl.

A particular value for $E^2$ or $E^3$ when it is halogeno is, for example, fluoro, chloro, bromo or iodo; and when it is alkoxy is, for example, methoxy, ethoxy or propoxy.

A particular value for $E^2$ when it is alkoxycarbonyl is, for example, methoxycarbonyl, ethoxycarbonyl or propoxycarbonyl; when it is alkenyloxycarbonyl is, for example, allyloxycarbonyl, 2-methyl-2-propenyloxycarbonyl or 3-methyl-3-butenyloxycarbonyl; when it is alkanoyl is, for example, formyl, acetyl or butyryl; when it is alkylthio is, for example, methylthio or ethylthio; when it is alkylsulphinyl is, for example, methylsulphinyl or ethylsulphinyl; and when it is alkylsulphonyl is, for example, methylsulphonyl or ethylsulphonyl.

Particular values for $E^4$ or $E^5$ include, by way of example, for alkyl: methyl and ethyl; for alkyl containing one or more fluoro substituents: fluoromethyl, trifluoromethyl, 2,2,2-trifluoroethyl and pentafluoroethyl; for alkoxy: methoxy and ethoxy; for halogeno: chloro, bromo and iodo; for alkoxycarbonyl: methoxycarbonyl, ethoxycarbonyl and propoxycarbonyl; for alkenyloxycarbonyl: allyloxycarbonyl, 2-methyl-2-propenyloxycarbonyl and 3-methyl-3-butenyloxycarbonyl; for alkanoyl: formyl, acetyl or butyryl; for N-alkylcarbamoyl: N-methyl and N-ethylcarbamoyl; and for di(N-alkyl)carbamoyl: N,N-dimethylcarbamoyl and N,N-diethylcarbamoyl.

A particular value for Rc when it is alkyl is, for example, methyl or ethyl.

A particular value for Ra or for an optional substituent which may be present on a phenyl moiety of $R^1$, $R^2$, $T^1$, $T^2$, $T^3$ or $E^2$ include, by way of example, for alkyl: methyl and ethyl; for alkoxy: methoxy and ethoxy; and for halogeno: chloro, bromo and iodo.

A particular value for $G^1$, $G^2$, $G^3$ or $G^4$ includes, by way of example, methyl, ethyl, propyl, methoxy, ethoxy, chloro, bromo or iodo, especially when one or more of $G^1$, $G^2$, $G^3$ and $G^4$ is attached at a position ortho to the group X.

A value for $R^1$, $T^1$ or $T^3$ of particular interest is, for example, methyl, ethyl or propyl.

A value for $R^2$ of particular interest is, for example, hydrogen.

A value for $T^2$ of particular interest is, for example, alkoxycarbonyl or, when $T^3$ and $T^4$ form alkylene is, for example, halogeno.

A value for $T^4$ of particular interest is, for example, alkoxycarbonyl or halogeno.

A value of particular interest for $T^3$ and $T^4$ when together they form alkylene is, for example, trimethylene or tetramethylene.

A value for Y of particular interest is, for example, a group of the formula —NRb— in which Rb is hydrogen.

A value for linking group A of formula IIc of particular interest is, for example, an optionally substituted group of the formula —CH=CH—, —CH=CH—CO— or —CH$_2$—CH$_2$—CO—.

A value of particular interest for $E^1$ is, for example, methyl or ethyl; for $E^2$ is, for example, hydrogen; for $E^3$ is, for example, methyl, ethyl or halogeno; for $E^4$ is, for example, halogeno; and for $E^5$ is, for example, methyl.

A value of particular interest for Q when it is a group of the partial structural formula IIa includes, for example, 2-methyl-quinolin-4-yloxy and 2-ethylquinolin-4-yloxy; when it is a group of the partial structural formula IIb includes, for example, 3-methoxycarbonyl-2,6-dimethylpyridin-4-yloxy, 2,6-diethyl-3-methoxycarbonylpyridin-4-yloxy, 6-ethyl-3-methoxycarbonyl-2-methylpyridin-4-yloxy, 2-ethyl-5,6,7,8-tetrahydroquinolin-4-yloxy, 3-chloro-2,6-diethylpyridin-4-ylamino, 3-bromo-2,6-diethylpyridin-4-yl and 2,6-diethyl-3-iodopyridin-4-ylamino; and when it is a group of the partial structural formula IIc includes, for example, 4-chloro-2,6-dimethyl-1H-pyrrolo[3,2-c]-pyridin-1-yl, 5,7-dimethyl-2-oxo-1,2-dihydro-1,6-naphthyridin-1-yl, 5,7-diethyl-2-oxo-1,2-dihydro-1,6-naphthyridin-1-yl, 5,7-dimethyl-2-oxo-1,2,3,4-tetrahydro-1,6-naphthyridin-1-yl and 5,7-diethyl-2-oxo-1,2,3,4-tetrahydro-1,6-naphthyridin-1-yl.

A preferred value for $G^1$, $G^2$, $G^3$ or $G^4$ is, for example, hydrogen.

A preferred value for X is, for example, oxygen or —NH—.

A preferred value for Z is, for example, carboxy or 1H-tetrazol-5-yl.

Preferably the group Q—CH$_2$— is linked at the para position relative to X.

A combination of values of special interest is, for example, when $R^1$ and $R^3$ are both alkyl, when $T^1$ and $T^3$ are both alkyl or when $T^1$ is alkyl and $T^3$ together with $T^4$ form alkylene.

A particular group of compounds of the formula I which are of interest comprises compounds of the formula I as defined above but excluding those compounds wherein one or both of $E^4$ and $E^5$ is selected from carbamoyl, N-alkylcarbamoyl and di-(N-alkylcarbamoyl) of up to 7 carbon atoms, phenyl, pyridyl, phenylthio, phenylsulphinyl and phenylsulphonyl; or a non-toxic salt thereof.

Particular groups of compounds of the invention comprise those compounds of the formula I in which Q constitutes:

(1) a group of the partial structural formula IIa in which ring B, $R^1$, $R^2$, $R^3$ and $R^4$ have any of the values defined hereinbefore;

(2) a group of the partial structural formula IIb in which $T^1$, $T^2$, $T^3$, $T^4$ and Y have any of the values defined hereinbefore; and (3) a group of the partial structural formula IIc in which $E^1$, $E^2$, $E^3$, $E^4$, $E^5$ and linking group A have any of the values defined hereinbefore;

and wherein in each of said groups the variables $G^1$, $G^2$, $G^3$, $G^4$, X and Z have any of the values defined hereinbefore; together with the non-toxic salts thereof.

Sub-groups of compounds of the invention of special interest from within the groups of compounds of particular interest (1) to (3) above comprise those compounds of the formula I in which Q constitutes:

(a) a group of the partial structural formula IIa wherein ring B together with the pyridine ring to which it is attached constitutes a quinoline ring;

(b) a group of the partial structural formula IIa wherein ring B together with the pyridine ring to which it is attached constitutes a pyrido-pyridine ring (that is a naphthyridine);

(c) a group of the partial structural formula IIb wherein Y is an oxygen atom;

(d) a group of the partial structural formula IIb wherein Y is a group of the formula —NH—;

(e) a group of the partial structural formula IIc wherein linking group A together with the nitrogen atom and pyridine ring to which it is attached constitutes a 1,6-naphthyrid-2(1H)-one ring; and (f) a group of the partial structural formula IIc wherein linking group A together with the nitrogen atom and pyridine ring to which it is attached constitutes a 1H-pyrrolo[3,2-c]pyridine ring; and wherein in each of said groups $R^1$, $R^2$, $R^3$, $R^4$, $T^1$, $T^2$, $T^3$, $T^4$, $E^1$, $E^2$, $E^3$, $E^4$ and $E^5$, where present have any of the values defined above and the variables $G^1$, $G^2$, $G^3$, $G^4$, X and Z have any of the values defined hereinbefore; together with the non-toxic salts thereof.

A preferred group of compounds of the invention comprises those compounds of the formula I wherein Q is a group of partial structural formula IIc in which linking group A is unsubstituted and together with the nitrogen atom and pyridine ring to which linking group A is attached constitutes a 1,6-naphthyridin-2(1H)-one or 1,2,3,4-tetrahydro-1,6-naphthyridin-2-one ring; $E^1$ is (1–4C)alkyl; $E^2$ is hydrogen; $E^3$ is (1–4C)alkyl; X is oxygen or —NH—; Z is carboxy or 1H-tetrazol-5-yl; and $G^1$, $G^2$, $G^3$, $G^4$ are independently selected from any of the values defined hereinbefore; together with the non-toxic salts thereof.

Preferred compounds of the formula I from within those contained in groups (1), (2) or (3) or within subgroups (a), (b), (c), (d), (e) or (f) above are those wherein the group Q—$CH_2$— is attached at the para position relative to X. Of these, those compounds in which X is oxygen are particularly preferred.

Compounds of the invention which are of particular interest include, for example, the specific embodiments set out hereinafter in the accompanying Examples. Of these, the compounds of formula I described in Examples 2, 3, 4 and 5 are of special interest and these compounds, or a non-toxic salt thereof, are provided as a further feature of the invention.

It will be appreciated that the formula I compounds can form salts with suitable acids or bases. Particularly suitable non-toxic salts for such compounds include, for example, salts with bases affording physiologically acceptable cations, for example, alkali metal (such as sodium and potassium), alkaline earth metal (such as magnesium and calcium), aluminium and ammonium salts, as well as salts with suitable organic bases, such as with ethanolamine, methylamine, diethylamine or triethylamine, as well as salts with acids forming physiologically acceptable anions, such as salts with mineral acids, for example with hydrogen halides (such as hydrogen chloride and hydrogen bromide), sulphuric and phosphoric acid, and with strong organic acids, for example with p-toluenesulphonic and methanesulphonic acids.

The compounds of formula I may be obtained by standard procedures of organic chemistry well known in the art for the production of structurally analogous compounds. Such procedures are provided as a further feature of the invention and include, by way of example, the following procedures in which the generic radicals have any of the values given above, unless stated otherwise:

a) For those compounds in which Z is carboxy, a carboxylic acid derivative of the formula III, in which W is a protected carboxy group selected from (1–6C)alkoxycarbonyl (especially methoxy-, ethoxy-, propoxy- or t-butoxy-carbonyl), phenoxycarbonyl, benzyloxycarbonyl and carbamoyl, is converted to carboxy.

The conversion may be carried out, for example by hydrolysis, conveniently in the presence of a suitable base such as an alkali metal hydroxide, for example, lithium, sodium or potassium hydroxide. The hydrolysis is generally carried out in the presence of a suitable aqueous solvent or diluent, for example in an aqueous (1–4C)alkanol, such as aqueous methanol or ethanol. However, it may also be performed in a mixture of an aqueous and non-aqueous solvent such as water and toluene using a conventional quaternary ammonium phase transfer catalyst. The hydrolysis is generally performed at a temperature in the range, for example, 0°–120° C., depending on the reactivity of the group W. In general, when W is carbamoyl, temperatures in the range, for example, 40°–120° C. are required to effect the hydrolysis.

Alternatively, when W is benzyloxycarbonyl the conversion may also be performed by hydrogenolysis, for example using hydrogen at 1–3 bar in the presence of a suitable catalyst, such as palladium on charcoal or on calcium sulphate, in a suitable solvent or diluent such as a (1–4C)alkanol (typically ethanol or 2-propanol) and at a temperature in the range, for example, 0°–40° C.

Further, when W is t-butoxycarbonyl, the conversion may also be carried out by hydrolysis at a temperature in the range, for example, 0°–100° C., in the presence of a strong acid catalyst, such as trifluoroacetic acid. The hydrolysis may either be performed in an excess of the acid or in the presence of a suitable diluent such as tetrahydrofuran, t-butyl methyl ether or 1,2-dimethoxyethane.

b) For those compounds of formula I wherein Z is tetrazolyl, a compound of the formula IV in which $P^1$ is a suitable protecting group, such as trityl, benzhydryl, trialkyltin (for example trimethyltin or tributyltin) or triphenyltin, affixed to a nitrogen of the tetrazolyl moiety, is deprotected.

The reaction conditions used to carry out the deprotection necessarily depend on the nature of the group $P^1$. As an illustration, when it is trityl, benzhydryl, trialkyltin or triphenyltin, the decomposition conditions include, for example, acid catalysed hydrolysis in a mineral acid (such as aqueous hydrochloric acid), conveniently in an aqueous solvent (such as aqueous dioxan, methanol or 2-propanol). Alternatively, a trityl or benzhydryl group may be removed by hydrogenolysis, for example as described in (a) above for conversion of a benzyloxycarbonyl to a carboxy.

Compounds of the formula IV wherein $p^1$ is trialkyltin or triphenyltin may be obtained, for example, by reaction of a nitrile of the formula VII with a trialkyltin azide, such as tributyltin azide, or triphenyltin azide respectively. The reaction is conveniently carried out in a suitable solvent or diluent, such as toluene or xylene, and at a temperature in the range, for example, 50°–150° C. Nitriles of the formula VII may be obtained, for example, by alkylation of a compound of the formula Q.H with a nitrile of the formula VIII wherein Hal. stands for a suitable leaving group such as chloro, bromo, iodo, methanesulphonyloxy or p-toluenesulphonyloxy, using similar conditions to those used in process (c) described hereinafter. The necessary compounds of formula VIII may be made by standard procedures such as those described in Scheme 7, or by analogy therewith. Alternatively, the nitriles of the formula VII may be obtained from stepwise conversion of a compound of formula I wherein Z is a carboxy group or a compound of the formula III under standard conditions. Additionally, a nitrile of the formula VII wherein Q is a group of the partial structural formula IIb in which Y is the group —NRb— and Rb is alkanoyl or benzoyl may be obtained from the corresponding compound wherein Rb is hydrogen by acylation or benzoylation under standard conditions.

It will be appreciated that procedures (a) and (b) may be carried out with a compound of the formula III or IV respectively in which one or more functional groups of Q and X are protected with suitable protecting groups. For example, when X is an imino (—NH—) group it may be protected with a suitable nitrogen protecting group such as an acyl group (for example acetyl, trichloroacetyl or trifluoroacetyl) or an alkyloxycarbonyl group (for example tert-butyloxycarbonyl). The protecting groups may be removed either during the carrying out of procedure (a) or (b), dependent on the conditions employed, or subsequent thereto using conventional techniques. For example, a tert-butyloxycarbonyl group used to protect X when it is imino may be removed by base hydrolysis, using for example an alkali metal hydroxide (such as sodium hydroxide) in a suitable solvent (such as methanol or ethanol) and at a temperature in the range of 0° to 100° C., preferably 75° C. to ambient temperature.

c) A compound of the formula Q.H (or a tautomer thereof) is alkylated with a compound of the formula V wherein Hal. stands for a suitable leaving group such as chloro, bromo, iodo, methanesulphonyloxy or p-toluenesulphonyloxy.

The reaction is preferably carried out in the presence of a suitable base, for example, an alkali metal alkoxide such as sodium or potassium methoxide, ethoxide or tert-butoxide, an alkali metal hydride such as sodium hydride, or an alkali metal carbonate such as sodium or potassium carbonate, or an organic base such as diisopropylethylamine or 4-dimethylaminopyridine. The reaction is conveniently carried out in a suitable solvent or diluent, for example, a (1–4C)alkanol such as methanol or ethanol, an ether such as tetrahydrofuran or dioxan, or a polar solvent such as N,N-dimethylformamide or N-methylpyrrolidone and at a temperature in the range, for example, 10°-100° C. In carrying out process (c), about two molecular equivalents of a suitable base is generally required.

It will be appreciated that it may be necessary to carry out procedure (c) with a starting material of formula V and/or Q.H in which one or more functional groups present are protected with suitable protecting groups. It will also be appreciated that procedure (c) is suitable for the production of the starting materials of formula III for the reaction described in (a) above if a compound of the formula Va is used in place of a formula V compound. Similarly, using an analogous procedure, but starting with the appropriate compound of the formula VI, the starting materials of the formula IV may be obtained for procedure (b). The compounds of formula V, Va and VI may be obtained, for example, as illustrated in Scheme 7, or by analogy therewith.

Many of the compounds of formula Q.H (or the tautomers thereof) are already known and the remainder can be made by analogy therewith using standard procedures of organic chemistry well known in the art, for example as described in standard works of heterocyclic chemistry such as that edited by Elderfield. Certain 4-quinolones are described in EPA, Publication No. 412848 and certain 4-naphthyridones are described in International Patent Application No. PCT/GB90/01776. Certain 4-pyridones are described in EPA, Publication No. 453210 and 499416 and in *Monatshefte fur Chemie*, 1969, 100, 132; *J. Chem. Soc.* (B), 1968, 866; *Liebigs Ann. Chem.*, 1982, 1656; *Heterocycles*, 1982, 13, 239; and *J. Am. Chem. Soc.*, 1974, 96(4), 1152. Certain 4-aminopyridines are disclosed in EPA, Publication No. 499415 or may be obtained as described in *Tet. Lett.*, 1990, 3485 from intermediates obtainable as described in J. Het. Chem., 1989, 26, 1575 or European Patent No. 129408. Other compounds of the formula Q.H may be obtained as illustrated in Schemes 1 to 6.

Whereafter, those compounds of formula I wherein Z is 1H-tetrazol-5-yl may be obtained by stepwise conversion of a compound of the formula I wherein Z is a carboxy group, or a compound of the formula III, into the corresponding nitrile under standard conditions, followed by reaction of the nitrile with an azide such as an alkali metal azide, preferably in the presence of an ammonium halide, and preferably in the presence of a suitable polar solvent such as N,N-dimethylformamide and at a temperature in the range, for example, 50° to 160° C.

Whereafter, when a non-toxic salt of a compound of formula I is required, it may be obtained, for example, by reaction with the appropriate base affording a physiologically acceptable cation, or with the appropriate acid affording a physiologically acceptable anion, or by any other conventional salt formation procedure.

Further, when an optically active form of a compound of formula I is required, one of the aforesaid processes may be carried out using an optically active starting material. Alternatively, the racemic form of a compound of formula I in which Z is an acidic group may be resolved, for example by reaction with an optically active form of a suitable organic base, for example, ephedrine, N,N,N-trimethyl-(1-phenylethyl)ammonium hydroxide or 1-phenylethylamine, followed by conventional separation of the diastereoisomeric mixture of salts thus obtained, for example by fractional crystallisation from a suitable solvent, for example a (1–4C)alkanol, whereafter the optically active form of said compound of formula I may be liberated by treatment with acid using a conventional procedure, for example using an aqueous mineral acid such as dilute hydrochloric acid.

Certain of the intermediates defined herein are novel, for example the compounds of the formula III, IV, VII and VIII, and are provided as a further feature of the invention.

As stated above, the compounds of formula I will have beneficial pharmacological effects in warm-blooded animals (including man) in diseases and medical conditions where amelioration of the vasoconstrictor and fluid retaining properties of the renin-angiotensin-aldosterone system is desirable, at least in part by antagonism of one or more of the physiological actions of AII. The compounds of the invention will thus be useful in the treatment of diseases or medical conditions such as hypertension, congestive heart failure and/or hyperaldosteronism in warm-blooded animals (including man), as well as in other diseases or medical conditions in which the renin-angiotensin-aldosterone system plays a significant causative role.

The antagonism of one or more of the physiological actions of AII and, in particular, the antagonism of the interaction of AII with the receptors which mediate its effects on a target tissue, may be assessed using one or more of the following, routine laboratory procedures:

Test A

This in vitro procedure involves the incubation of the test compound initially at a concentration of 100 micromolar (or less) in a buffered mixture containing fixed concentrations of radiolabelled AII and a cell surface membrane fraction prepared from a suitable angiotensin target tissue. In this test, the source of cell surface membranes is the guinea pig adrenal gland which is well known to respond to AII. Interaction of the radiolabelled AII with its receptors (assessed as radiolabel bound to the particulate membrane fraction following removal of unbound radiolabel by a rapid filtration procedure such as is standard in such studies) is antagonized by compounds which also bind to the membrane receptor sites and the degree of antagonism (observed in the test as displacement of membrane-bound radioactivity) is determined readily by comparing the receptor-bound radioactivity in the presence of the test compound at the specified test concentration with a control value determined in the absence of the test compound. Using this procedure compounds showing at least 50% displacement of radiolabelled AII binding at a concentration of $10^4$M are retested at lower concentrations to determine their potency. For determination of the $IC_{50}$ (concentration for 50% displacement of radiolabelled AII binding), concentrations of the test compound are ordinarily chosen to allow testing over at least four orders of magnitude centred about the predicted approximate $IC_{50}$, which latter is subsequently determined from a plot of percentage displacement against concentration of the test compound.

In general, the compounds of formula I as defined above show significant inhibition in Test A at a concentration of 50 micromolar or much less. By way of illustration, the compound of Example 2 gave an $IC_{50}$ of $2.7 \times 10^{-7}$M.

Test B

This in vitro test involves the measurement of the antagonistic effects of the test compound against AII-induced contractions of isolated rabbit aorta, maintained in a physiological salt solution at 37° C. In order to ensure that the effect of the compound is specific to antagonism of AII, the effect of the test compound on noradrenaline-induced contractions may also be determined in the same preparation.

In general, the compounds of formula I as defined above show significant inhibition in Test B at a final concentration of 50 micromolar or much less.

Test C

This in vivo test involves using terminally-anaesthetised or conscious rats in which an arterial catheter has been implanted under anaesthesia for the measurement of changes in blood pressure. The AII antagonistic effects of the test compound following oral or parenteral administration, are assessed against angiotensin II-induced pressor responses. To ensure that the effect is specific, the effect of the test compound on vasopressin-induced pressor responses may also be determined in the same preparation.

The compounds of formula I generally show specific AII-antagonist properties in Test C at a dose of 50 mg/kg body weight or much less, without any overt toxicological or other untoward pharmacological effect.

Test D

This in vivo test involves the stimulation of endogenous AII biosynthesis in a variety of species including rat, marmoset and dog by introducing a diet of low sodium content and giving appropriate daily doses of a saluretic known as furosemide. The test compound is then administered orally or parenterally to the animal in which an arterial catheter has been implanted under anaesthesia for the measurement of changes in blood pressure.

In general compounds of formula I will show AII-antagonist properties in Test D as demonstrated by a significant reduction in blood pressure at a dose of 50 mg/kg body weight or much less, without any overt toxicological or other untoward pharmacological effect.

The compounds of formula I will generally be administered for therapeutic or prophylactic purposes to warm-blooded animals (including man) requiring such treatment in the form of a pharmaceutical composition, as is well known in the pharmaceutical art. According to a further feature of the invention there is provided a pharmaceutical composition comprising a compound of formula I, or a salt thereof, as defined above, together with a pharmaceutically acceptable diluent or carrier. Such compositions will conveniently be in a form suitable for oral administration (e.g. as a tablet, capsule, solution, suspension or emulsion) or parenteral administration (e.g. as an injectable aqueous or oily solution, or injectable emulsion).

The compounds of formula I may also be advantageously administered for therapeutic or prophylactic purposes together with another pharmacological agent known in the general art to be of value in treating one or more of the diseases or medical conditions referred to hereinabove.

In general a compound of formula I (or a pharmaceutically acceptable salt thereof as appropriate) will generally be administered to man so that, for example, a daily oral dose of up to 50 mg/kg body weight (and preferably of up to 10 mg/kg) or a daily parenteral dose of up to 5 mg/kg body weight (and preferably of up to 1 mg/kg) is received, given in divided doses as necessary, the precise amount of compound (or salt) administered and the route and form of administration depending on size, age and sex of the person being treated and on the particular disease or medical condition being treated according to principles well known in the medical arts.

In addition to their aforesaid use in therapeutic medicine in humans, the compounds of formula I are also useful in the veterinary treatment of similar conditions affecting commercially valuable warm-blooded animals, such as dogs, cats, horses and cattle. In general for such treatment, the compounds of the formula I will generally be administered in an analogous amount and manner to those described above for administration to humans. The compounds of formula I are also of value as pharmacological tools in the development and standardisation of test systems for the evaluation of the effects of AII in laboratory animals such as cats, dogs, rabbits, monkeys, rats and mice, as part of the continuing search for new and improved therapeutic agents.

The invention will now be illustrated by the following non-limiting Examples in which, unless otherwise stated:

(i) concentrations and evaporations may be carried out by rotary evaporation in vacuo;

(ii) operations are carried out at room temperature, that is in the range 18°–26° C.;

(iii) flash column chromatography is performed on Merck Kieselgel 60 (Art. no. 9385) obtained from E Merck, Darmstadt, Germany;

(iv) yields, where given, are intended for the assistance of the reader only and are not necessarily the maximum attainable by diligent process development;

(v) $^1$H NMR spectra were determined at 200 MHz in CDCl$_3$ or d$_6$-dimethylsulphoxide (d$_6$-DMSO) using tetramethylsilane (TMS) as an internal standard, and are expressed as chemical shifts (delta values) in parts per million relative to TMS using conventional abbreviations for designation of major peaks: s, singlet; m, multiplet; t, triplet; br, broad; d, doublet;

(vi) the term "1,6-naphthyrid-2(1H)-one is equivalent to the term "1,2-dihydro-1,6-naphthyridin-2-one"; and (vii) all end-products have satisfactory microanalyses.

EXAMPLE 1

1M Sodium hydroxide solution (0.90 ml) was added to a solution of ethyl 2-[4-((2-ethyl-5,6,7,8-tetrahydroquinolin-4-yl)oxymethyl)phenoxy]phenylacetate (A) (200 mg) in ethanol (4.5 ml) and the solution was left to stand for 5 hours. Volatile material was removed by evaporation and the residue was dissolved in water (10 ml). The solution was neutralised with 1M acetic acid (0.90 ml) to precipitate 2-[4-((2-ethyl-5,6,7,8-tetrahydroquinolin-4-yl)oxymethyl)phenoxy]phenylacetic acid (130 mg), m.p. 129°–134° C.; NMR: 1.05(t, 3H), 1.6–1.8(m, 4H), 2.5–2.6(m, 2H), 2.7(q, 2H), 2.8–2.9(m, 2H), 5.1(s, 2H), 5.55(s, 1H), 7.05(d, 2H), 7.15–7.45(m, 5H), 7.7(d, 2H); mass spectrum (positive fast atom bombardment (+ve FAB), DMSO/m-nitrobenzyl alcohol (NBA)): 418 (M+H)+; microanalysis, found: C, 72.4; H, 6.6; N, 3.1%; $C_{26}H_{27}NO_4 \cdot 0.75H_2O$ requires: C, 72.4; H, 6.6; N, 3.1%.

The starting material (A) was obtained as follows:

(i) p-Cresol (4.45 g) was added portionwise over 30 minutes to a stirred suspension of sodium hydride (60% dispersion in mineral oil; 1.81 g) in N,N-dimethylformamide (DMF) (80 ml). When evolution of hydrogen ceased, ethyl-α-bromophenylacetate (10.0 g) was added and the mixture was left to stand for 20 hours. Water (500 ml) was added and the mixture was extracted with ethyl acetate (2×250 ml). The extracts were washed with water (250 ml), followed by saturated sodium chloride solution (250 ml) and then dried (MgSO₄). Volatile material was removed by evaporation and the residue was purified by flash chromatography, eluting with ethyl acetate/hexane (1:19 v/v), to give ethyl 2-(4-methylphenoxy)phenylacetate (B) (6.7 g), as an oil; NMR (d₆-DMSO): 1.2(t, 3H), 2.15(s, 3H), 4.1(q, 2H), 5.9(s, 1H), 7.2–7.6(m, 9H).

(ii) N-Bromosuccinimide (6.64 g) and azo(bisisobutyronitrile) (400 mg) were added to a solution of compound (B) (10.1 g) in carbon tetrachloride (100 ml). The mixture was heated under reflux for 20 hours and then cooled to ambient temperature. Insoluble material was removed by filtration and the filtrate was concentrated. The residue was purified by flash chromatography eluting with ethyl acetate/hexane (1:19 v/v), to give ethyl 2-(4-bromomethylphenoxy)phenylacetate (C) (5.9 g), as an oil; NMR (d₆-DMSO): 1.15(t, 3H), 4.1(q, 2H), 4.65(s, 2H), 6.0(s, 1H), 6.95(d, 2H), 7.3–7.5(m, 5H), 7.5–7.6(m, 2H).

(iii) A solution of 2-ethyl-4-(1H)-quinolone (obtained from aniline and methyl propionylacetate using an analogous procedure to that described in Org. Syn., 1955, Coll Vol III, pages 374 and 593, m.p. 178°–181° C.) (30 g) in glacial acetic acid (300 ml) was catalytically hydrogenated over platinum oxide (3.0 g). The catalyst was removed by filtration through diatomaceous earth and the filtrate was concentrated. Toluene (250 ml) was added to the residue and the solution re-evaporated. The resulting oil was triturated with ether to give 2-ethyl-5,6,7,8-tetrahydro-4(1H)-quinolone (D) (22.6 g), m.p. 226°–227° C.; NMR: 1.2(t, 3H), 1.65–1.85(m, 4H), 2.5–2.7(m, 6H), 6.1(s, 1H), 12.3(br s, 1H).

(iv) Sodium hydride (60% dispersion in mineral oil; 63 mg) was added to a solution of compound D (254 mg) in DMF (5 ml). When evolution of hydrogen ceased, a solution of compound C (500 mg) in DMF (5 ml) was added and the solution was left to stand for 20 hours. Water (50 ml) was added and the mixture was extracted with ethyl acetate (2×25 ml). The combined extracts were washed with water (25 ml), followed by saturated sodium chloride solution (25 ml) and then dried (MgSO₄). The solvent was removed by evaporation and the residue purified by flash chromatography, eluting with ethyl acetate/hexane (1:1 v/v), to give ethyl 2-[4-((2-ethyl-5,6,7,8-tetrahydroquinolin-4-yl)oxymethyl)phenoxy]phenylacetate (A) (265 mg), as an oil which solidified on standing, m.p. 89°–90° C. (after trituration with hexane); NMR: 1.1–1.35(2×t, 6H), 1.7–1.9(m, 4H), 2.6(t, 2H), 2.7(q, 2H), 2.85(t, 2H), 4.1–4.3(m, 2H), 5.0(s, 2H), 5.6(s, 1H), 6.5(s, 1H), 7.0(d, 2H), 7.25–7.5(m, 5H), 7.55–7.65(m, 2H).

EXAMPLE 2

Using an analogous procedure to that described in Example 1, but starting from ethyl 2-[4-((5,7-diethyl-2-oxo-1,2-dihydro-1,6-naphthyridin-1-yl)methyl)phenoxy]phenylacetate (A), there was obtained in 43% yield (2-[4-((5,7-diethyl-2-oxo-1,2-dihydro-1,6-naphthyridin-1-yl)methyl)phenoxy]phenylacetic acid, m.p. 211°–215° C.; NMR (d₆-DMSO): 1.15(t, 3H), 1.25(t, 3H), 2.7(q, 2H), 3.05(q, 2H), 5.4(s, 2H), 5.65(s, 1H), 6.7(d, 1H), 6.9(d, 2H), 7.1(s, 1H), 7.15(d, 2H), 7.25–7.4(m, 3H), 7.45–7.55(m, 2H), 8.2(d, 1H); mass spectrum (+ve FAB, DMSO/NBA): 443(M+H)+; microanalysis, found: C, 69.2; H, 6.0; N, 5.9%; $C_{27}H_{26}N_2O_4 \cdot 1.5H_2O$ requires C, 69.1; H, 6.2; N, 6.0%.

The starting material (A) was obtained as follows:

(i) A solution of tin tetrachloride (24 ml) in toluene (70 ml) was added to a stirred solution of 3-amino-2-pentenenitrile (1.0 g) (obtained as described in J. Het. Chem., 1989, 26, 1575) and methyl propionylacetate (13.4 g) in toluene (150 ml). The mixture was heated at reflux for 6 hours and then stirred at ambient temperature for 16 hours. Saturated sodium carbonate solution was added to the stirred mixture until the aqueous phase was basic (pH>9). Ether (200 ml) was added to the mixture and the precipitated tin salts removed by filtration through diatomaceous earth. The organic phase of the filtrate was separated, washed with sodium chloride solution and dried (MgSO₄). Solvent was removed by evaporation and the residue was extracted with hot hexane (3×50 ml). The combined hexane extracts were evaporated and the residue was dissolved in minimum of hot hexane. The solution was then cooled at 4° C. for 16 hours when a yellow solid crystallised. The solid (7.3 g) was collected by filtration and purified by flash chromatography eluting with dichloromethane/methanol (1:19 v/v) to give methyl 4-amino-2,6-diethylpyridine-3-carboxylate (B) (6 g) as a light yellow solid, m.p. 75° C.; NMR (CDCl₃): 1.25(t,6H), 2.65(q,2H), 2.95(q,2H), 3.9(s,3H), 5.65(broad s,2H), 6.25(s,1H); mass spectrum (chemical ionisation, ammonia): 209(M+H)+.

(ii) Methyl 4-amino-2,6-diethylpyridine-3-carboxylate (B) (3.94 g) was added to a mixture of 2M sodium hydroxide solution (9.5 ml) and methanol (40 ml) and the mixture was heated at reflux for 16 hours. The solution was cooled to ambient temperature and volatile material was removed by evaporation. The residue was partitioned between ethyl acetate and a mixture of 2M hydrochloric acid (9.5 ml) and water (20 ml). The aqueous phase was separated, water was removed by evaporation and the residue was extracted with ethyl acetate/methanol (1:1 v/v). The combined organic extracts were filtered and solvent was removed from the filtrate by evaporation to give 4-amino-2,6-diethylpyridine-3-carboxylic acid (C) (3.46 g) as a yellow-brown foam; NMR (d₆-DMSO): 1.18(m,6H), 2.64(q,2H), 3.12(q,2H), 6.49(s,1H), 8.28(broad s,2H); mass spectrum (chemical ionisation, ammonia): 195(M+H)+.

(iii) 4-Amino-2,6-diethylpyridine-3-carboxylic acid (C) (3.26 g) was heated at 220° C. for 50 minutes. The residue was cooled to ambient temperature and purified by flash chromatography eluting with concentrated aqueous ammonia solution/dichloromethane/methanol (1:85:15 v/v) to give 4-amino-2,6-diethylpyridine (D) (1.94 g) as a solid, m.p. 133°-137° C.; NMR (CDCl₃/d₆-DMSO): 1.24(t,6H), 2.68(q,4H), 4.48(broad s,2H), 6.27(s,2H); mass spectrum (chemical ionisation, ammonia): 151(M+H)+.

(iv) 4-Amino-2,6-diethylpyridine (D) (1.8 g) was added to a solution of iodine (3.1 g) and [bis(trifluoroacetoxy)iodo]benzene (5.7 g) in a mixture of dichloromethane (70 ml) and methanol (20 ml) and the mixture was stirred for 16 hours. Solvent was removed by evaporation and the residue was partitioned between ethyl acetate and a mixture of saturated sodium metabisulphite solution (50 ml) and saturated sodium carbonate solution (150 ml). The organic phase was separated, washed with saturated sodium chloride solution and dried (MgSO₄). Solvent was removed by evaporation and the residue was purified by flash chromatography eluting with dichloromethane/methanol (97:3 v/v) to give 4-amino-2,6-diethyl-3-iodopyridine (E) (1.33 g) as a solid, m.p. 72°-74° C.; NMR (CDCl₃): 1.25(m,6H), 2.65(q,2H), 2.96(q,2H), 4.59(broad s,2H), 6.30(s,1H); mass spectrum (chemical ionisation, ammonia): 277(M+H)+.

(v) Palladium (II) acetate (50 mg) and tri(2-methylphenyl)phosphine (50 mg) were added to a solution of 4-amino-2,6-diethyl-3-iodopyridine (E) (1.3 g), ethyl acrylate (1.2 ml) and triethylamine (1.2 ml) in DMF (25 ml). The mixture was heated at 130° C. for 2 hours and then allowed to cool. Volatile material was removed by evaporation and the residue was purified by flash chromatography, eluting with aqueous ammonia (density 0.88 g/ml)/dichloromethane/methanol (1:200:20, v/v/v) to give ethyl-3-[(4-amino-2,6-diethyl) pyridin-3-yl]acrylate (G), as an oil; NMR (CDCl₃): 1.15-1.45(m,9H), 2.7(q,2H), 2.8(q,2H), 4.25(q,2H), 4.5(broad s,2H), 6.25(d,2H), 7.75(d,2H); mass spectrum (chemical ionisation, ammonia): 249 (M+H)+.

(vi) A solution of ethyl-3-[(4-amino-2,6-diethyl)pyridin-3-yl]acrylate (G) (600 mg) in dry methanol (10 ml) was added to a solution of sodium methoxide, prepared from sodium (500 mg) and dry methanol (30 ml), and the mixture was heated at reflux under an atmosphere of argon for 3 hours. Solvent was removed by evaporation and the residue partitioned between ethyl acetate and water. The aqueous phase was separated and extracted with ethyl acetate. The combined organic solutions were washed with saturated sodium chloride solution and then dried (MgSO₄). The solvent was removed by evaporation and the residue was triturated with ether to give 5,7-diethyl-1,6-naphthyridin-2(1H)-one (H) (310 mg), as a solid, m.p. 170°-171° C.; NMR (CDCl₃): 1.45(m,6H), 2.85(q,2H), 3.1(q,2H), 6.7(d, 1H), 6.95(s,1H), 8.05(d, 1H), 12.05(broad s,1H): mass spectrum (chemical ionisation, ammonia): 203(M+H)+.

(vii) A mixture of compound H (404 mg), ethyl 2-(4-bromomethylphenoxy)phenylacetate (700 mg) and potassium carbonate (552 mg) in 1,2-dimethoxyethane (10 ml) was heated under reflux for 1 hour. Insoluble material was removed by filtration and the filtrate was concentrated. The residue was purified by flash chromatography, eluting with ethyl acetate/hexane (7:3 v/v) to give ethyl 2-[4-((5,7-diethyl-2-oxo-1,2-dihydro-1,6-naphthyridin-1-yl)methyl)phenoxy]phenylacetate (A) (390 mg), as a gum; NMR (CDCl₃): 1.2(t, 3H), 1.25(t, 3H), 1.35(t, 3H), 2.8(q, 2H), 3.1(q, 2H), 4.1-4.25(m, 2H), 5.4(s, 2H), 5.55(s, 1H), 6.7(d, 1H), 6.85(s, 1H), 6.9(d, 2H), 7.15(d, 2H), 7.3-7.4(m, 3H), 7.5-7.6(m, 2H), 7.95(d, 1H).

EXAMPLE 3

Using an analogous procedure to that described in Example 1, but starting from methyl 2-[4-((5,7-diethyl-2-oxo-1,2,3,4-tetrahydro-1,6-naphthyridin-1-yl)methyl)-phenoxy]phenyl acetate (A), there was thus obtained in 12% yield 2-[4-((5,7-diethyl-2-oxo-1,2,3,4-tetrahydro-1,6-naphthyridin-1-yl)methyl)phenoxy]phenylacetic acid, m.p. 122°-124° C.; NMR (d₆-DMSO): 1.1(t, 3H), 1.15(t, 3H), 2.5-2.6(m, 2H), 2.65-2.8(m, 4H), 2.85-2.95(m, 4H), 5.05(s, 2H), 5.75(s, 1H), 6.7(s, 1H), 6.9(d, 2H), 7.15(d, 2H), 7.3-7.45(m, 3H), 7.5(d, 2H); mass spectrum (+ve FAB, DMSO/NBA): 445 (M+H)+.

The starting material A was obtained as follows:

(i) Using an analogous procedure to that described in Example 1, part (i), but starting from methyl-α-bromophenylacetate, there was obtained in 75% yield methyl 2-(4-methylphenoxy)phenylacetate (B) as an oil; NMR: 2.3(s, 3H), 3.7(s, 3H), 5.6(s, 1H), 6.7(d, 2H), 7.05(d, 2H), 7.2-7.4(m, 3H), 7.5-7.6(m, 2H).

(ii) Using an analogous procedure to that described in Example 1, part (ii), but starting from compound B, there was obtained in 59% yield methyl 2-(4-bromomethylphenoxy)phenylacetate (C) as an oil; NMR: 3.75(s, 3H), 4.5(s, 1H), 5.65(s, 1H), 6.9(d, 2H), 7.3(d, 1H), 7.3-7.45(m, 3H), 7.5-7.6(m, 2H).

(iii) A mixture of compound C (2.34 g), 5,7-diethyl-1,2,3,4-tetrahydro-1,6-naphthyridin-2-one (1.02 g), potassium t-butoxide (0.57 g) and 1,4,7,10,13,16-hexaoxacyclooctadecane (132 mg) in dry tetrahydrofuran (50 ml) was heated under reflux for 36 hours. Saturated sodium chloride solution (100 ml) was added and the mixture was extracted with ether (2×100 ml). The combined extracts were dried (MgSO₄) and concentrated by evaporation. The residue was purified by flash chromatography, eluting with ethyl acetate/hexane (3:7 v/v), to give methyl 2-[4-((5,7-diethyl-2-oxo-1,2,3,4-tetrahydro-1,6-naphthyridin-1-yl)methyl)phenoxy]phenylacetate (A) (0.41 g) as an oil; NMR (d₆-DMSO): 1.05-1.25(2×t, 6H), 2.45-2.9(m, 8H), 3.6(s, 3H), 5.0(s, 2H), 5.95(s, 1H), 6.5-7.5(m, 10H).

5,7-diethyl-1,2,3,4-tetrahydro-1,6-naphthyridin-2-one, used in step (iii), was obtained as follows:

A solution of 5,7-diethyl-1,6-naphthyridin-2(1H)-one (10.0 g) in ethanol (100 ml) was catalytically hydrogenated over 10% palladium on carbon (1 g) at 50° C. and a pressure of 20 atmospheres for 30 hours. The catalyst was removed by filtration through diatomaceous earth and the filtrate was concentrated under vacuum to give 5,7-diethyl-1,2,3,4-tetrahydro-1,6-naphthyridin-2-one (9.6 g), m.p. 90°-94° C.; NMR: 1.2-1.3(m, 6H), 2.6-2.85(m, 6H), 3.05(t, 2H), 6.5(s, 1H), 8.9(br s, 1H).

EXAMPLE 4

Using an analogous procedure to that described in Example 1, but starting from methyl 2-[4-((5,7-diethyl-2-oxo-1,2-dihydro-1,6-naphthyridin-1-yl)methyl-2-propylphenoxy]phenylactate (A), there was obtained in 23% yield 2-[4-((5,7-diethyl-2-oxo-1,2-dihydro-1,6-naphthyridin-1-yl)methyl-2-propylphenoxy]phenylacetic acid, m.p. 148°–150° C.; NMR (d6-DMSO): 0.8(t, 3H), 1.15(t, 3H), 1.25(t, 3H), 1.45–1.7(m, 2H), 2.5–2.6(m, 2H), 2.7(q, 2H), 3.0(q, 2H), 5.35(s, 2H), 5.4(s, 1H), 6.7(d, 1H), 6.75(d, 1H), 6.9(d, 1H), 7.1(d, 2H), 7.2–7.35(m, 3H), 7.5(d, 2H), 8.15(d, 1H); mass spectrum (+ve FAB, MeOH/NBA): 485 (M+H)+.

The starting material A was obtained as follows:

(i) A solution of methyl 4-(t-butyldimethylsilyloxy)-3-(2-propen-1-yl)benzoate (14.4 g) (obtained as described in International patent application, publication no. WO 91/11999) in methanol (280 ml) was catalytically hydrogenated over 10% palladium on carbon (2.9 g) at 3 atmospheres pressure for 2 hours. The catalyst was removed by filtration through diatomaceous earth and the filtrate was concentrated by evaporation. The residue was purified by flash chromatography, eluting with ethyl acetate/hexane (1:3 v/v), to give methyl 4-(t-butyldimethylsilyloxy)-3-propylbenzoate (B) (11.7 g) as an oil; NMR: 0.25(s, 6H), 0.95(t, 3H), 1.0(s, 9H), 1.5–1.7(m, 2H), 2.6(t, 2H), 3.9(s, 3H), 6.8(d, 1H), 7.8(dd, 1H), 7.8(s, 1H).

(ii) Lithium borohydride (1.77 g) was added to a solution of compound B (10.0 g) in dry tetrahydrofuran (150 ml) and the mixture was heated under reflux for 24 hours. The mixture was allowed to cool and then acidified to pH 2 with 2M hydrochloric acid. Ethyl acetate (300 ml) was added and the organic layer was separated, washed with saturated sodium chloride solution (100 ml) and dried (MgSO4). Volatile material was removed by evaporation and the residue was purified by flash chromatography, eluting with ethyl acetate/hexane (1:3 v/v) to give 4-(t-butyldimethylsilyloxy)-3-propylbenzyl alcohol (C) (5.1 g) as an oil; NMR: 0.15(s, 6H), 0.85(t, 3H), 0.9(s, 9H), 1.4–1.6(m+brs, 3H), 2.5(t, 2H), 4.5(s, 2H), 6.65(d, 1H), 6.95(d, 1H), 7.05(s, 1H).

(iii) A solution of triphenylphosphine (5.8 g) in dichloromethane (25 ml) was added over a period of 30 minutes to a stirred solution of compound C (5.0 g) and carbon tetrabromide (7.3 g) in dichloromethane (50 ml) at 0° C. under an atmosphere of argon. The solution was kept at 0° C. for 45 minutes and then allowed to warm to ambient temperature. The solution was applied to a silica gel flash chromatography column and eluted with dichloromethane to give 4-(t-butyldimethylsilyloxy)-3-propylbenzyl bromide as an oil; NMR: 0.25(s, 6H), 1.0(t, 3H), 1.05(s, 9H), 1.5–1.7(m, 2H), 2.6(t, 2H), 4.5(s, 2H), 6.75(d, 1H), 7.1(d, 1H), 7.2(s, 1H).

(iv) Potassium t-butoxide (0.62 g) was added to a stirred solution of 5,7-diethyl-1,6-naphthyridin-2(1H)-one (1.01 g) in dry tetrahydrofuran (20 ml). The mixture was stirred for 10 minutes and then a solution of 1,4,7,10,13,16-hexacyclooctadecane (145 mg) and compound D (2.32 g) in tetrahydrofuran (5 ml) was added. The mixture was stirred for 18 hours and then saturated sodium chloride solution (50 ml) was added. The mixture was extracted with ethyl acetate (2×25 ml) and the extracts were dried (MgSO4). Volatile material was removed by evaporation and the residue was purified by flash chromatography, eluting with ethyl acetate/hexane (1:3 v/v), to give 1-[4-(t-butyldimethylsilyloxy)-3-propylbenzyl]-5,7-diethyl-1,6-naphthyridin-2(1H)-one (E) (0.95 g), m.p. 103°–105° C.; NMR: 0.15(s, 6H), 0.9(t, 3H), 1.0(s, 9H), 1.2(t, 3H), 1.3(t, 3H), 1.45–1.6(m, 2H), 2.5(t, 2H), 2.75(q, 2H), 3.05(q, 2H), 5.4(s, 2H), 6.5–6.75(m, 2H), 6.85(d, 1H), 6.9(s, 1H), 7.0(d, 1H), 7.9(d, 1H).

(v) 1.0M Tetrabutylammonium fluoride in tetrahydrofuran (2 ml) was added to a stirred solution of compound E (0.9 g) in tetrahydrofuran (8 ml) under an atmosphere of argon. The solution was left to stand for 2 hours and then volatile material was removed by evaporation. The residue was purified by flash chromatography, eluting with ethyl acetate, to give 5,7-diethyl-1-(4-hydroxy-3-propylbenzyl)-1,6-naphthyridin-2(1H)-one (F) (0.54 g) as a foam; NMR: 0.9(t, 3H), 1.2(t, 3H), 1.3(t, 3H), 1.55–1.65(m, 2H), 2.55(t, 2H), 2.8(q, 2H), 3.1(q, 2H), 5.4(s, 2H), 5.5(br s, 1H), 6.65(d, 1H), 6.75(d, 1H), 6.9(d, 1H), 6.95(s, 1H), 7.05(s, 1H), 7.95(d, 1H).

(vi) Sodium hydride (60% dispersion in oil, 51 mg) was added to a solution of compound F (440 mg) in tetrahydrofuran (15 ml) under an atmosphere of argon. The mixture was stirred for 20 minutes and then methyl α-bromophenylacetate (320 mg) in tetrahydrofuran (5 ml) was added. The mixture was stirred for 18 hours and then volatile material was removed by evaporation. The residue was partitioned between ethyl acetate (25 ml) and water (25 ml) and the organic layer was separated, washed with saturated sodium chloride solution (25 ml) and dried (MgSO4). Volatile material was removed by evaporation and the residue was purified by flash chromatography, eluting with methanol/dichloromethane (1:199 v/v) to give methyl 2-[4-((5,7-diethyl-2-oxo-1,2-dihydro-1,6-naphthyridin-1-yl)methyl)-2-propylphenoxy]phenylacetate (A) (300 mg) as an oil; NMR: 0.9(t, 3H), 1.2(t, 3H), 1.35(t, 3H), 1.55–1.7(m, 2H), 2.7(t, 2H), 2.8(q, 2H), 3.1(q, 2H), 5.4(s, 2H), 5.6(s, 1H), 6.65(d, 1H), 6.75(d, 1H), 6.9(s, 1H), 6.95(d, 1H), 7.1(s, 1H), 7.3–7.4(m, 3H), 7.5–7.6(m, 2H), 7.95(d, 1H).

EXAMPLE 5

1M Aqueous sodium hydroxide solution (2 ml) was added to a solution of methyl 2-[4-((5,7-diethyl-2-oxo-1,2-dihydro-1,6-naphthyridin-1-yl)methyl)-phenylamino]phenylacetate (A) (68 mg) in methanol (20 ml) and the mixture was stirred for 16 hours. Volatile material was removed by evaporation and the residue was partitioned between ethyl acetate (10 ml) and water (10 ml). The aqueous layer was separated and acidified with glacial acetic acid. The precipitated product was extracted with ethyl acetate (3×25 ml) and the combined extracts were washed with water (5 ml) and dried (MgSO4). Volatile material was removed by evaporation and the residue was dissolved in ethyl acetate and ethereal hydrogen chloride was added. The precipitated solid was collected and dried under high vacuum to give 2-[4-((5,7-diethyl-2-oxo-1,2-dihydro-1,6-naphthyridin-1-yl)methyl)phenylamino]phenylacetic acid dihydrochloride (64 mg) as a pale yellow solid, m.p. 174°–178° C.; NMR (d6-DMSO): 1.2–1.35(m, 6H), 2.99(q, 2H), 3.32(q, 2H), 4.03(q, 1H), 5.05(s, 1H), 5.37(s, 2H), 6.6(d, 2H), 6.93(d, 1H), 7.03(d, 2H), 7.2–7.4(m, 3H), 7.45(d, 2H), 7.65(s, 1H), 8.33(d, 1H); mass spectrum (+ve FAB, MeOH/NBA): 442 (M+H)+; microanalysis, found: C, 61.1; H, 5.8; N, 7.8; $C_{27}H_{27}N_3O_3.2HCl.H_2O$ requires: C, 61.0; H, 5.8; N, 7.9%.

The starting material (A) was obtained as follows:

(i) Sodium hydride (50% dispersion in oil; 0.2 g) was added to a stirred solution of 5,7-diethyl-1,6-naphthyridin-2(1H)-one (1.0 g) in DMF (10 ml) under argon. The mixture was stirred for 15 minutes, then 4-nitrobenzyl bromide (1.1 g) was added and the mixture was stirred for 16 hours. The reaction mixture was poured into water (50 ml) and extracted with ethyl acetate (2×30 ml). The combined extracts were washed with saturated sodium chloride solution (10 ml), dried (MgSO$_4$) and the solvent was removed by evaporation. The residue was purified by flash chromatography eluting with ethyl acetate/dichloromethane (1:4 v/v) to give 5,7-diethyl-1-(4-nitrobenzyl)-1,6-naphthyridin-2(1H)-one (B) as yellow solid (1.4 g), m.p. 105°–106° C.; NMR (CDCl$_3$): 1.22(t, 3H), 1.36(t, 3H), 2.77(q, 2H), 3.11(q, 2H), 5.77(s, 2H), 6.69(s, 1H), 6.77(d, 1H), 7.38(d, 2H), 8.03(d, 1H), 8.19(d, 2H); mass spectrum (+ve CI): 338 (M+H)+; microanalysis, found: C, 67.0; H, 5.7; N, 12.4; C$_{19}$H$_{19}$N$_3$O$_3$ requires C, 67.6; H, 5.7; N, 12.5%.

(ii) A solution of compound B (16.0 g) in THF (200 ml) was cataltically hydrogenated over platinum (IV) oxide (320 mg) at one atmosphere for 3 hours. The catalyst was removed by filtration and the solvent was removed by evaporation to give 1-(4-aminobenzyl)-5,7-diethyl-1,6-naphthyridin-2(1H)-one (C) as an off white solid (14.5 g), m.p. 164°–165° C.; NMR (d$_6$-DMSO): 1.85(t, 3H), 1.2(t, 3H), 2.72(q, 2H), 3.03(q, 2H), 5.1(s, 2H), 5.28(s, 2H), 6.48(d, 2H), 6.66(d, 1H), 6.94(d, 2H), 7.14(s, 1H), 8.16(d, 1H); mass spectrum (+ve FAB, MeOH/DMSO/NBA): 308 (M+H)+; microanalysis, found: C, 74.0; H, 6.9; N, 13.1%; C$_{19}$H$_{21}$N$_3$O requires C, 74.2; H, 6.9; N, 13.1 %.

(iii) Potassium carbonate (2.76 g) was added to a stirred solution of compound C (1.22 g) and methyl 2-bromo-2-phenylacetate (0.916 g) in DMF (7 ml) and the mixture placed under an argon atmosphere. The reaction mixture was heated at 60° C. for 4 hours, then allowed to cool to ambient temperature. Water (50 ml) added and the mixture was extracted with ethyl acetate (50 ml). The organic phase was washed with water (2×50 ml), dried (MgSO$_4$) and the solvent removed by evaporation. The residue was recrystallised from methanol to give methyl 2-[4-((5,7-diethyl-2-oxo-1,2-dihydro-1,6-naphthyridin-1-yl)-methyl)phenylamino]phenylacetate (A) (1.02 g) as a pale yellow solid, m.p. 91°–92° C.; NMR (d$_6$-DMSO): 1.16(t, 3H), 1.23(t, 3H), 2.71(q, 2H), 3.2(d, 1H), 3.35(q, 2H), 3.61(s, 3H), 5.18(d, 1H), 5.28(s, 2H), 6.6(complex m, 3H), 6.98(d, 2H), 7.14(s, 1H), 7.28–7.48(m, 5H), 8.16(d, 1H); mass spectrum (+ve FAB CI): 456 (M+H)+; microanalysis, found: C, 72.1; H, 6.4; N, 8.9%; C$_{28}$H$_{29}$N$_3$O$_3$.0.5H$_2$O requires: C, 72.3; H, 6.4; N, 9.0%.

EXAMPLE 6 (Note: all parts by weight)

The compounds of the invention may be administered for therapeutic or prophylactic use to warm-blooded animals such as man in the form of conventional pharmaceutical compositions, typical examples of which include the following:

| a) Capsule (for oral administration) | |
|---|---|
| Active ingredient* | 20 |
| Lactose powder | 578.5 |
| Magnesium stearate | 1.5 |
| b) Tablet (for oral administration) | |
| Active ingredient* | 50 |
| Microcrystalline cellulose | 400 |
| Starch (pregelatinised) | 47.5 |
| Magnesium stearate | 2.5 |
| c) Injectable Solution (for intravenous administration) | |
| Active ingredient* | 0.05–1.0 |
| Propylene glycol | 5.0 |
| Polyethylene glycol (300) | 3.0–5.0 |
| Purified water | to 100% |
| d) Injectable Suspension (for intramuscular administration) | |
| Active ingredient* | 0.05–1.0 |
| Methylcellulose | 0.5 |
| Tween 80 | 0.05 |
| Benzyl alcohol | 0.9 |
| Benzalkonium chloride | 0.1 |
| Purified water | to 100% |

Note:
the active ingredient* may typically be an Example described hereinbefore and may conveniently be present as a pharmaceutically acceptable acid-addition salt, such as the hydrochloride salt. Tablets and capsules formulations may be coated in conventional manner in order to modify or sustain dissolution of the active ingredient. Thus, for example, they may be coated with a conventional enterically digestible coating.

Chemical Formulae

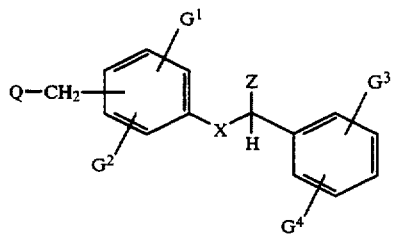

I

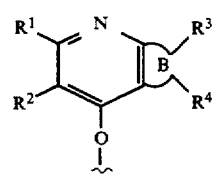

IIa

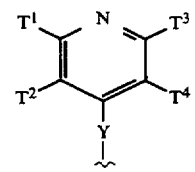

IIb

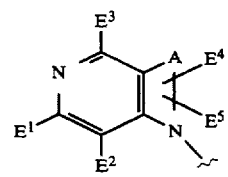

IIc

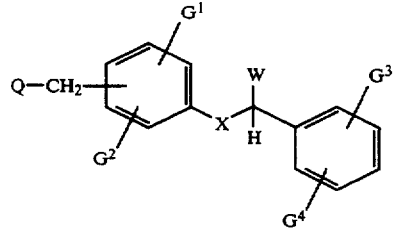

III

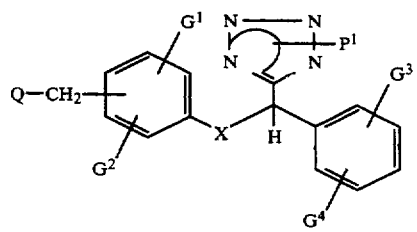

IV

-continued
Chemical Formulae
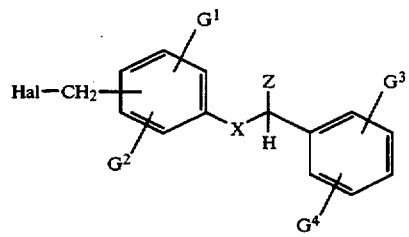
V
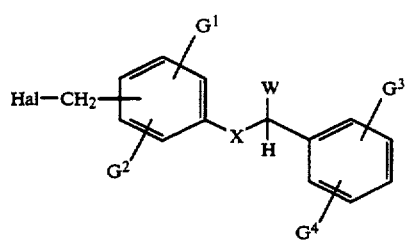
Va
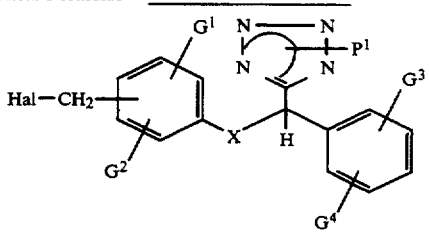
VI
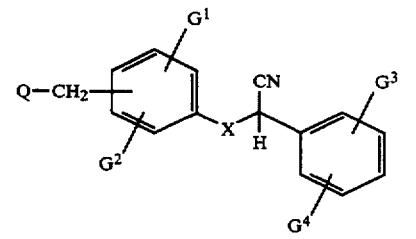
VII
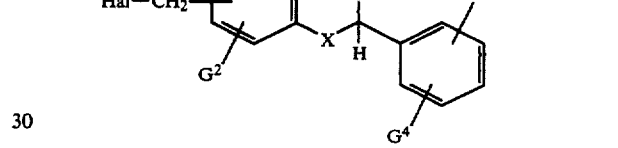
VIII
Scheme 1
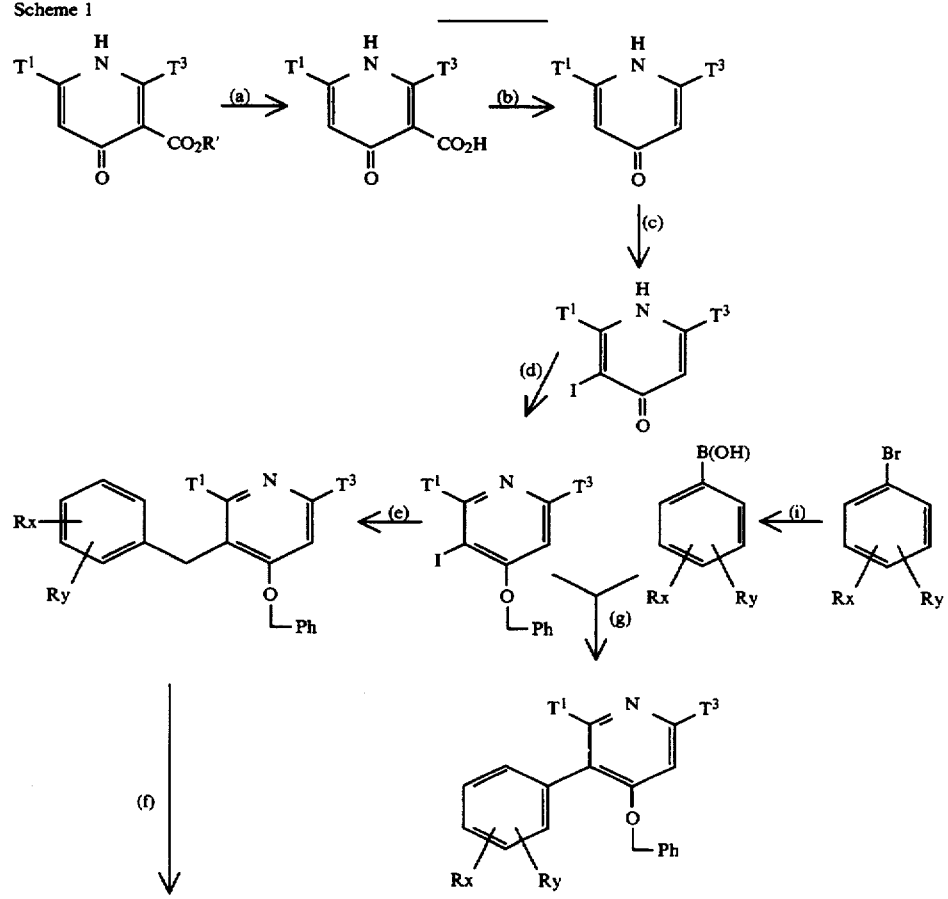

Scheme 1

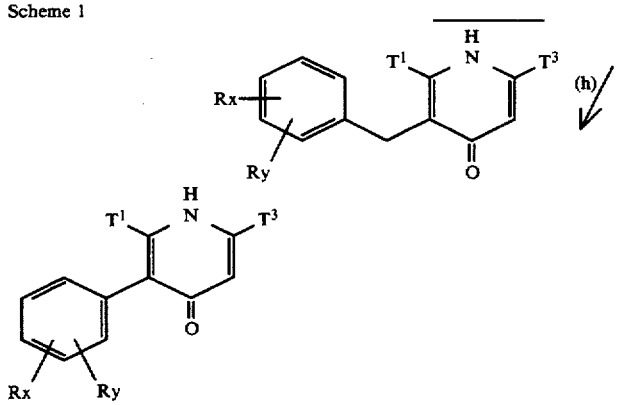

Note:
$T^1=T^3$=methyl or ethyl; Rx and Ry are optional substituents;
Ph=phenyl; R'=lower alkyl Reagents:
a) NaOH, methanol, water, reflux
b) Sublimation at 250°C.
c) Iodine, NaOH, water
d) $C_6H_5CH_2Cl$, NaH, DMF, 50° C.
e) Product from (d) added to $(Rx)(Ry)PhCH_2ZnBr$ in THF(from activated zinc, $(Rx)(Ry)PhCH_2Br$ in THF), then $(Ph_3P)_4Pd$
f) hydrogenation over palladium on carbon, methanol
g) $(Ph_3P)_4Pd$, methanol, aq. $NaHCO_3$, toluene, reflux
h) ammonium formate, 10% palladium on carbon, methanol
i) tert-ButylLi/pentane; trimethyl borate/THF/−78° C.; aq.HCl Scheme 2

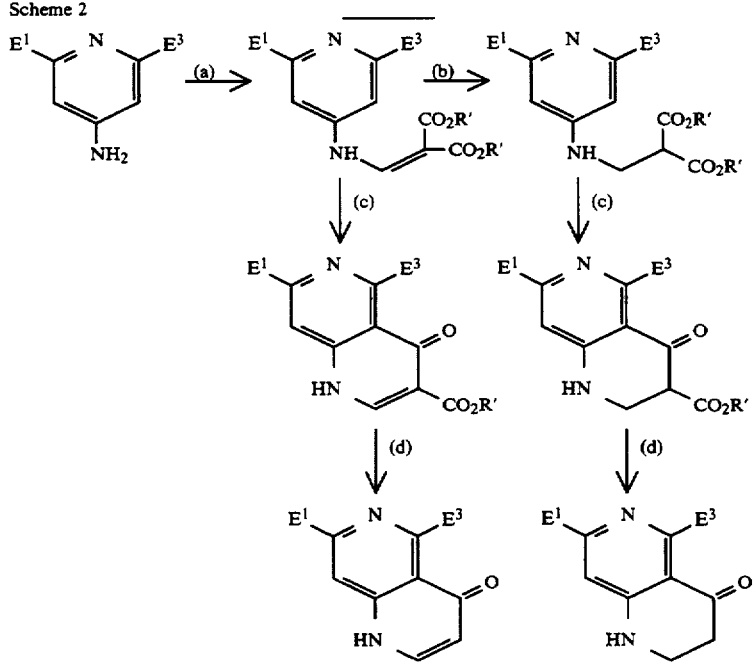

Note:

R'=lower alkyl

Reagents:

a) $R'OCH=C(CO_2R')_2$, 110° C.

b) hydrogen, Pd on C or $PtO_2$ c) Ph—Ph/Ph—O—Ph mixture, reflux

Scheme 2 d) (i) NaOH; (ii) as for step (c)

Scheme 2

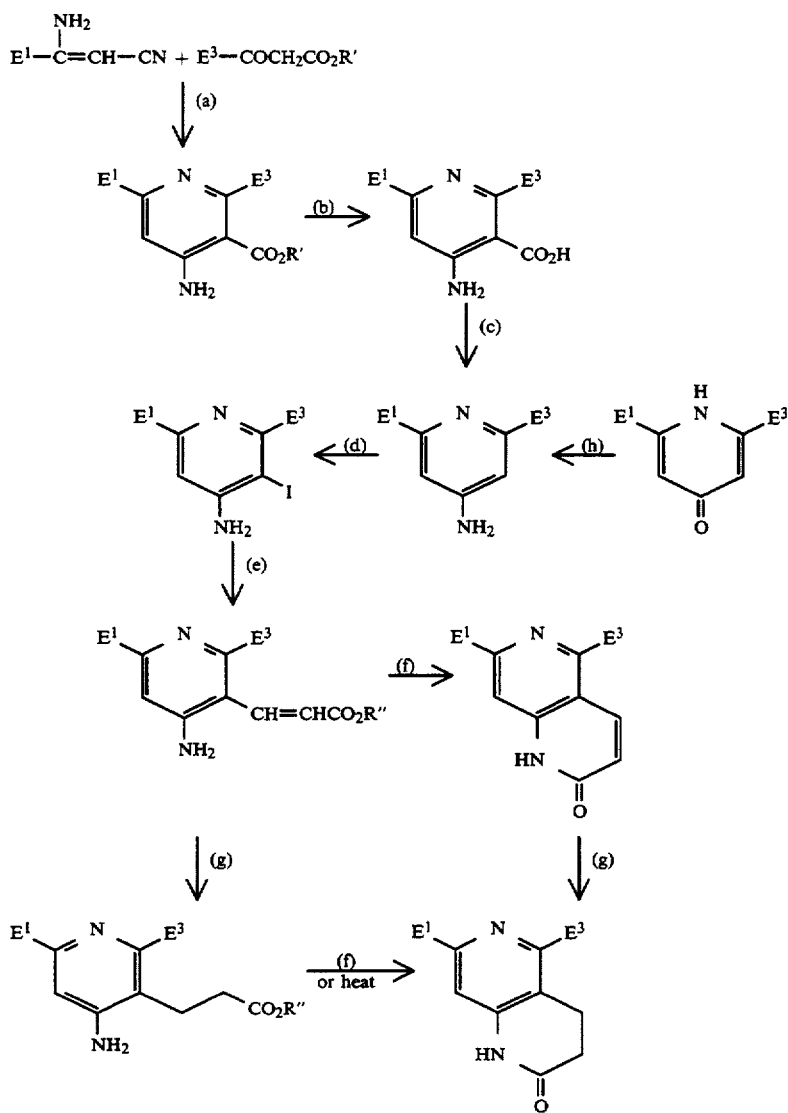

Note:

R′=lower alkyl; R″=lower alkyl

Reagents:

a) tin tetrachloride, toluene, reflux b) aqu. NaOH, methanol, reflux; then HCl c) heat, 220° C.

d) N-iodosuccinimide, dioxane e) Pd(II)acetate, Ph₃P, Et₃N, DMF, 130° C., CH$_2$=CHCO$_2$R″ f) NaOMe, methanol, reflux g) hydrogen, Pd on C or PtO$_2$, ethanol or ethanol/acetic acid, 1-30 atmospheres, 0-100° C.

h) (i) p-toluenesulphonyl isocyanate, CH$_3$CN, reflux (ii) conc. sulphuric acid, 50° C.

Scheme 3a

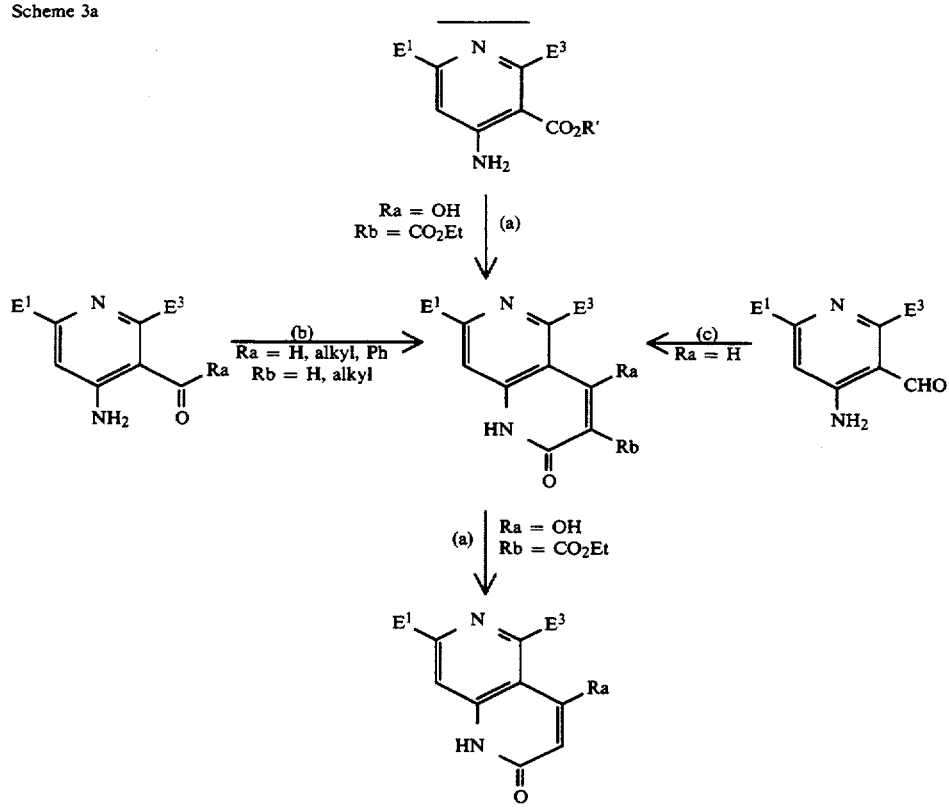

Note:
Et = ethyl; R' = lower alkyl
Reagents:
a) diethyl malonate, NaOEt, EtOH, 150° C, autoclave
b) Ph₃P=C(Rb)CO₂Et, xylene or toluene, reflux
c) RbCH₂CO₂Et(e.g.Rb=CO₂Et,Ph,Pyridyl,CN,SPh),EtOH
piperidine,reflux
d) aqu.HCl,dioxan,reflux Scheme 4

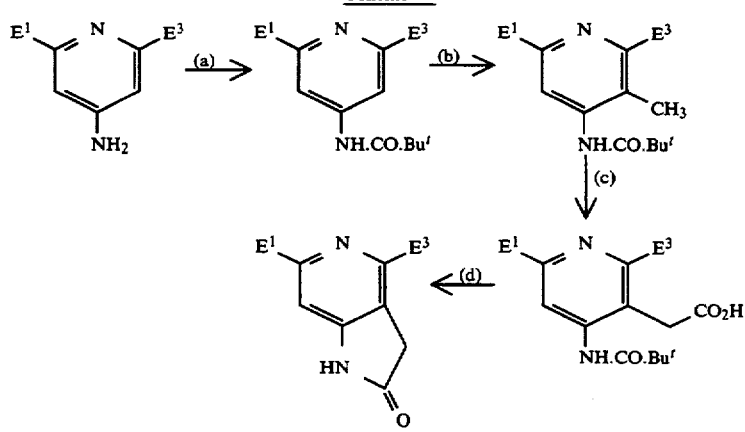

Reagents:
a) 1-(tert-butyl.CO)imidazole, toluene, heat
b) (i) tert-butyllithium (2 equivalents), −78° C., THF;
 (ii) iodomethane
c) as (b)(i); then carbon dioxide
d) aqueous HCl, heat Scheme 5

Note: R' and R" = lower alkyl;
Reagents:
(a) NaOMe, heat
(b) (i) NaOH (ii) HCl (iii) heat
(c) hydrazine hydrate, 2-ethoxyethanol, reflux; then acetone, reflux
(d) Ph—Ph/Ph—O—Ph mixture, reflux
(e) POCl$_3$, PCl$_5$, heat
(f) POCl$_3$ (freshly distilled), reflux
(g) (CH$_3$)$_3$OBF$_4$, dichloromethane Scheme 5a Scheme 5a

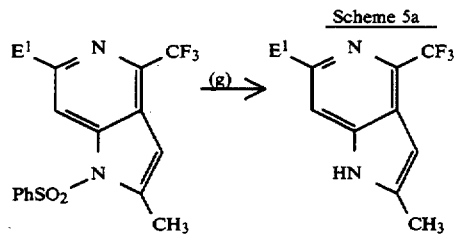

Note: Ph = phenyl
Reagents:
(a) POCl$_3$/DMF
(b) Catalytic hydrogenation over palladium on carbon
(c) N-Chlorosuccinimide, dichloromethane
(d) (i) n-BuLi, THF/hexane, −78 to 0° C.
    (ii) PhSO$_2$Cl, THF, −78 to ambient
(e) NaI, aqueous HI, methyl ethyl ketone, reflux
(f) CuI, KF, triethyl(trifluoromethyl)silane, DMF/NMP, 80° C.
(g) NaOH, aqu. methanol, reflux Scheme 6

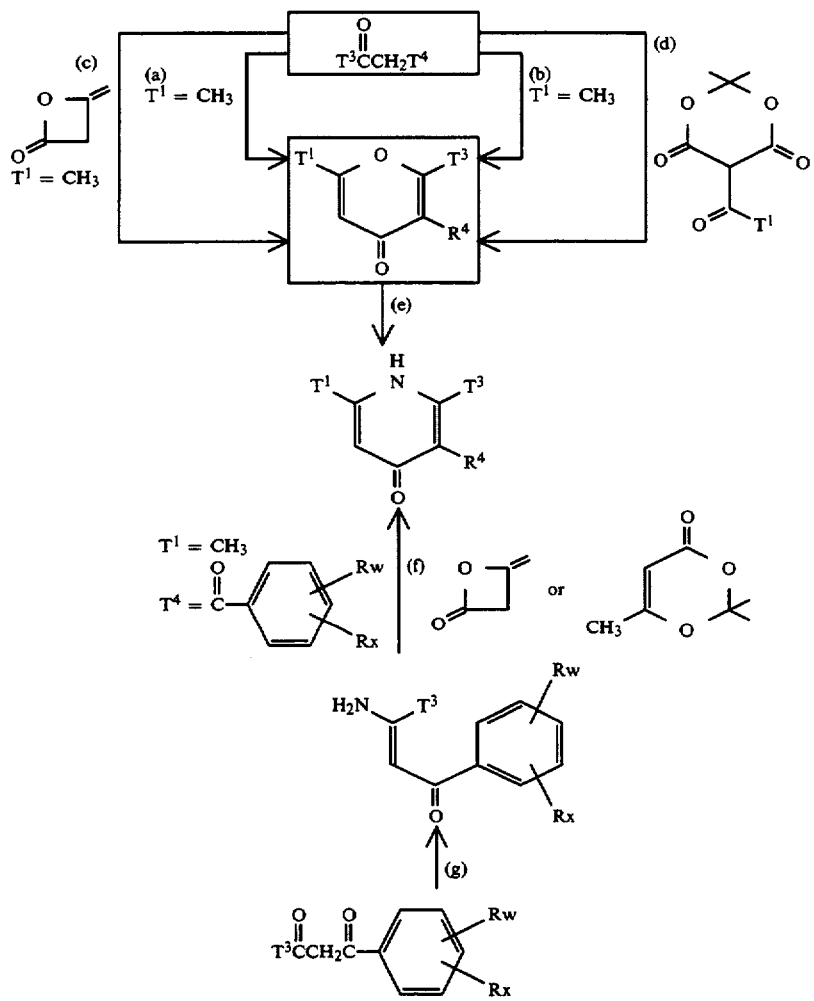

Note: Rw and Rx are optional substituents
Reagents:
(a) polyphosphoric acid, acetic acid
(b) (i) boron trifluoride, acetic anhydride
    (ii) NaH or (isopropyl)$_2$NLi, ethyl acetate
    (iii) benzene, PTSA, heat or conc. H$_2$SO$_4$, ambient temp.
(c) acetic acid, 0–50° C.
(d) heat, 120° C.
(e) ethanolic ammonia, 120° C., sealed tube -continued
Scheme 6
(f) heat
(g) ethanolic ammonia
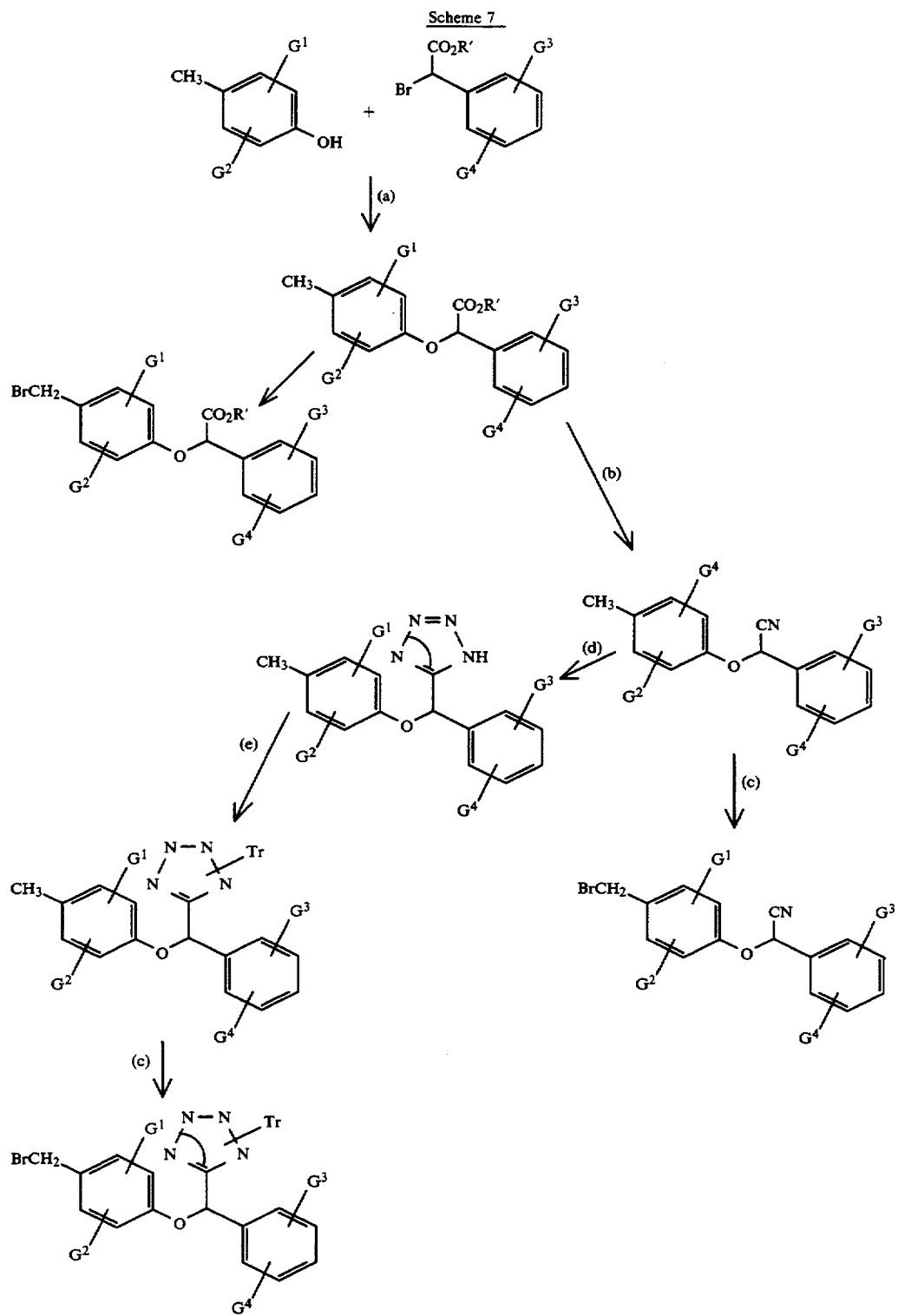
Note: R' = lower alkyl; Tr = triphenylmethyl (trityl)
Reagents:
a) NaH, DMF
b) (i) NH$_3$, methanol; (ii) POCL$_3$, Et$_3$N -continued Scheme 7 c) N-bromosuccinimide, azo(bisisobutyronitrile), CCl₄ d) Bu₃Sn.N₃/toluene; HCl/toluene e) Trityl chloride, Et₃N, CH₂Cl₂

What we claim is:

1. A heterocyclic compound of the formula I

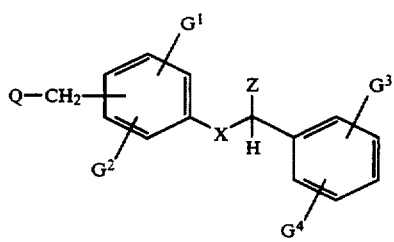

wherein

Q is selected from the partial structural formula [IIa or] IIc

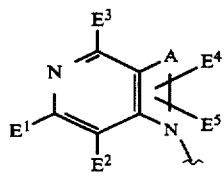

[in which ring B of formula IIa completes a pyridine ring;

R¹ is selected from (1-8C)alkyl, (3-8C)cycloalkyl, (3-8C)cycloalkyl-(1-4C)alkyl, phenyl, phenyl(1-4-C)alkyl or substituted (1-4C)alkyl, the latter containing one or more fluoro substituents or bearing an (1-4C)alkoxy substituent;

R² is selected from hydrogen, (1-8C)alkyl, (3-8C)cycloalkyl, (3-8C)cycloalkyl-(1-4C)alkyl, carboxy, (1-4C)alkoxycarbonyl, (3-6C)alkenyloxycarbonyl, cyano, nitro, phenyl or phenyl(1-4C)alkyl;

R³ and R⁴ are optional substituents on ring B independently selected from (1-4C)alkyl, (1-4C)alkoxy, halogeno, trifluoromethyl, cyano, nitro, fluoro(-1-4C)alkoxy, hydroxy or hydroxy(1-4C)alkyl;]

linking group A of formula IIc is selected from [—CH=CH—,]—CH=CH—CO—and [—CO—CH=CH—, —CO—CH₂—CH₂—, ] —CH₂—CH₂—CO—,[,—CH₂—CO— and —CO—CH₂—;]

E¹ is hydrogen, (1-8C)alkyl or trifluoromethyl;

E² is hydrogen, (1-8C)alkyl, halogeno, (1-4C)alkoxy, trifluoromethyl, carboxy, (1-4C)alkoxycarbonyl, (3-6C)alkenyloxycarbonyl, cyano, nitro, (1-4C)alkanoyl, (1-4C)alkyl S(O)ₘ— in which m is zero, 1 or 2, or phenylsulphonyl;

E³ is hydrogen, (1-8C)alkyl, (1-4C)alkoxy, halogeno or trifluoromethyl;

E⁴ and E⁵ are optional substituents on linking group A independently selected from (1-4C)alkyl, substituted (1-4C)alkyl containing one or more fluoro substituents, alkoxy, halogeno, cyano, nitro, carboxy, (1-4C)alkoxycarbonyl, (3-6C)alkenyloxycarbonyl, (1-4C)alkanoyl, carbamoyl. N-alkylcarbamoyl and di-(N-alkyl)carbamoyl of up to 7 carbon atoms, phenyl, pyridyl, phenylthio, phenylsulphinyl and phenylsulphonyl;

X is oxygen, sulphur or a group of the formula —NRc— wherein Rc is hydrogen or (1-4C)alkyl;

G¹, G², G³ and G⁴ are independently selected from hydrogen, (1-4C)alkyl, (1-4C)alkoxy and halogeno;

Z is 1H-tetrazol-5-yl, carboxy or a group of the formula —CONHSO₂Ra wherein Ra is (1-4C)alkyl or phenyl;

wherein any of said phenyl moieties of [any of said phenyl moieties of R¹, R² or ] E² may be unsubstituted or bear one or two substituents independently selected from (1-4C)alkyl, (1-4C)alkoxy, halogeno, cyano and trifluoromethyl;

or a non-toxic salt thereof.

2. A compound as claimed in claim 1 wherein ]R¹ is selected from methyl, ethyl, propyl, butyl, isobutyl, sec-butyl, pentyl, hexyl, cyclopropyl, cyclopentyl, cyclohexyl, cyclopropylmethyl, cyclopentylmethyl, cyclohexylmethyl, 2-cyclopentyl-ethyl, phenyl, benzyl, 1-phenylethyl, 2-phenylethyl, fluoromethyl, trifluoromethyl, 2,2,2-trifluoroethyl, pentafluoroethyl, 2-methoxyethyl and 2-ethoxyethyl;

R² is selected from hydrogen, methyl, ethyl, propyl, butyl, isobutyl, sec-butyl, pentyl, hexyl, cyclopropyl, cyclopentyl, cyclohexyl, cyclopropylmethyl, cyclopentylmethyl, cyclohexylmethyl, 2-cyclopentyl-ethyl, carboxy, methoxycarbonyl, ethoxycarbonyl, propoxycarbonyl, allyloxycarbonyl, 2-methyl-2-propenyloxycarbonyl, 3-methyl-3-butenyloxycarbonyl, cyano, nitro, phenyl, benzyl, 1-phenylethyl and 2-phenylethyl;

R³ and R⁴ are optional substituents on ring B independently selected from methyl, ethyl, methoxy, ethoxy, chloro, bromo, iodo, trifluoromethyl, cyano, nitro trifluoromethoxy, 2-fluoroethoxy, 2,2,2-trifluoroethoxy, 3,3,3-trifluoropropoxy, hydroxy, hydroxymethyl, 1-hydroxyethyl and 2-hydroxyethyl;]

E¹ is hydrogen, methyl, ethyl, propyl, butyl, isobutyl, sec-butyl, pentyl, hexyl or trifluoromethyl;

E² is hydrogen, methyl, ethyl, propyl, butyl, isobutyl, sec-butyl, pentyl, hexyl, fluoro, chloro, bromo, iodo, methoxy, ethoxy, propoxy, trifluoromethyl, carboxy, methoxycarbonyl, ethoxycarbonyl, propoxycarbonyl, allyloxycarbonyl, 2-methyl-2-propenyloxycarbonyl, 3-methyl-3-butenyloxycarbonyl, cyano, nitro, formyl, acetyl, butyryl, methylthio, ethylthio, methylsulphinyl, ethylsulphinyl, methylsulphonyl, ethylsulphonyl or phenylsulphonyl;

E³ is hydrogen, methyl, ethyl, propyl, butyl, isobutyl, sec-butyl, pentyl, hexyl, fluoro, chloro, bromo, iodo, methoxy, ethoxy, propoxy or trifluoromethyl;

E⁴ and E⁵ are optional substituents on linking group A independently selected from methyl, ethyl, fluoromethyl, trifluoromethyl, 2,2,2-trifluoroethyl, pentafluoroethyl, methoxy, ethoxy, chloro, bromo, iodo, cyano, nitro, carboxy, methoxycarbonyl, ethoxycarbonyl, propoxycarbonyl, allyloxycarbonyl, 2-methyl-2-propenyloxycarbonyl, 3-methyl-3- butenyloxycarbonyl, formyl, acetyl, butyryl, carbamoyl, N-methylcarbamoyl, N-ethylcarbamoyl, N,N-dimethylcarbamoyl, N,N-diethylcarbamoyl, phenyl, pyridyl, phenylthio, phenylsulphinyl and phenylsulphonyl;

X is oxygen, sulphur or a group of the formula —NRc wherein Rc is hydrogen, methyl or ethyl;

$G^1$, $G^2$, $G^3$ and $G^4$ are independently selected from hydrogen, methyl, ethyl, propyl, methoxy, ethoxy, chloro, bromo and iodo;

Ra is selected from methyl, ethyl and phenyl;

wherein any of said phenyl moieties of [any of said phenyl moieties of $R^1$, $R^2$ or ] $E^2$ may be unsubstituted or bear one or two substituents independently selected from methyl, ethyl, methoxy, ethoxy, chloro, bromo, iodo, cyano and trifluoromethyl; or a non-toxic salt thereof.

3. A compound of the formula I as claimed in claim 1 selected from (2-(4-((5,7-diethyl-2-oxo-1,2-dihydro-1,6-naphthyridin-1-yl)methyl)phenoxy)phenylacetic acid; 2-(4-((5,7-diethyl-2-oxo-1,2,3,4-tetrahydro-1,6-naphthyridin-1-yl)methyl)phenoxy)phenylacetic acid; 2-(4-((5,7-diethyl-2-oxo-1,2-dihydro-1,6-naphthyridin-1-yl)methyl-2-propylphenoxy)phenylacetic acid; and 2-(4-((5,7-diethyl-2-oxo-1,2-dihydro-1,6-naphthyridin-1-yl) methyl)phenylamino)phenylacetic acid; or a non-toxic salt thereof.

4. A compound as claimed in claim 1 but excluding those compounds wherein one or both of $E^4$ and $E^5$ is selected from carbamoyl, N-alkylcarbamoyl and di-(N-alkylcarbamoyl) of up to 7 carbon atoms, phenyl, pyridyl, phenylthio, phenylsulphinyl and phenylsulphonyl; or a non-toxic salt thereof.

5. A compound as claimed in claim 1 wherein Q is a group of partial structural formula IIc in which linking group A is unsubstituted and together with the nitrogen atom and pyridine ring to which linking group A is attached constitutes a 2-oxo-1,2-dihydro-1,6-naphthyridin-1-yl or 2-oxo-1,2,3,4-tetrahydro-1,6-naphthyridin-1-yl group.

6. A compound as claimed in claim 1 wherein Q is selected from [2-methyl-quinolin-4-yloxy, 2-ethylquinolin-4-yloxy, 3-methoxycarbonyl-2,6-dimethytpyridin-4-yloxy, 2,6-diethyl-3-methoxycarbonylpyridin-4-yloxy, 6-ethyl-3-methoxycarbonyl-2-methylpyridin-4-yloxy, 2-ethyl-5,6,7,8-tetrahydroquinolin-4-yloxy, 3-chloro-2,6-diethylpyridin-4-ylamino, 3-bromo-2,6-diethylpyridin-4-yl, 2,6-diethyl-3-iodopyridin-4-ylamino, 4-chloro-2,6-dimethyl-1H-pyrrolo(3,2-c)-pyridin-1-yl,] 5,7-dimethyl-2-oxo-1,2-dihydro-1,6-naphthyridin-1-yl, 5,7-diethyl-2-oxo-1,2-dihydro-1,6-naphthyridin-1-yl, 5,7-dimethyl-2-oxo-1,2,3,4-tetrahydro-1,6-naphthyridin-1-yl and 5,7-dimethyl-2-oxo-1,2,3,4-tetrahydro-1,6-naphthyridin-1-yl.

7. A salt as claimed in claim 1 which is selected from salts with acids forming physiologically acceptable anions and salts with bases forming physiologically acceptable cations.

8. A method for antagonising one or more of the actions of angiotensin II in a warm-blooded animal requiring such treatment which comprises administering to said animal an antagonistically effective amount of a compound of formula I, or a non-toxic salt thereof, as defined in claim 1.

9. A pharmaceutical composition which comprises a compound of the formula I, or a non-toxic salt thereof, as claimed in claim 1, together with a pharmaceutically acceptable diluent or carrier.

* * * * *